United States Patent
Ogino et al.

(10) Patent No.: US 12,048,415 B2
(45) Date of Patent: Jul. 30, 2024

(54) COLOR CORRECTION DEVICE FOR MEDICAL APPARATUS

(71) Applicant: DAI NIPPON PRINTING CO., LTD., Tokyo-to (JP)

(72) Inventors: Yoshihiko Ogino, Tokyo-to (JP); Tohru Sugiyama, Tokyo-to (JP); Yusuke Murayama, Tokyo-to (JP); Kiyoko Tateishi, Tokyo-to (JP); Akihiro Maeda, Tokyo-to (JP); Yoichi Kajimura, Tokyo-to (JP); Yutaka Matsumoto, Tokyo-to (JP)

(73) Assignee: DAI NIPPON PRINTING CO., LTD., Tokyo (JP)

( * ) Notice: Subject to any disclaimer, the term of this patent is extended or adjusted under 35 U.S.C. 154(b) by 330 days.

(21) Appl. No.: 17/430,127

(22) PCT Filed: Feb. 14, 2020

(86) PCT No.: PCT/JP2020/005770
§ 371 (c)(1),
(2) Date: Aug. 11, 2021

(87) PCT Pub. No.: WO2020/166697
PCT Pub. Date: Aug. 20, 2020

(65) Prior Publication Data
US 2022/0095891 A1  Mar. 31, 2022

(30) Foreign Application Priority Data
Feb. 14, 2019  (JP) .................. 2019-024677

(51) Int. Cl.
*A61B 1/00* (2006.01)
*A61B 1/04* (2006.01)
(Continued)

(52) U.S. Cl.
CPC .. *A61B 1/000094* (2022.02); *A61B 1/000095* (2022.02); *A61B 1/00045* (2013.01);
(Continued)

(58) Field of Classification Search
None
See application file for complete search history.

(56) References Cited

U.S. PATENT DOCUMENTS

2003/0234793 A1 * 12/2003 Stokes .................. H04N 9/64
  348/E9.037
2004/0024288 A1  2/2004 Uchikubo
(Continued)

FOREIGN PATENT DOCUMENTS

| CN | 101175433 A | 5/2008 |
| CN | 103444170 A | 12/2013 |

(Continued)

OTHER PUBLICATIONS

Pajevic, Sinisa, and Carlo Pierpaoli. "Color schemes to represent the orientation of anisotropic tissues from diffusion tensor data: application to white matter fiber tract mapping in the human brain." Magnetic Resonance in Medicine: An Official Journal of the International Society for Magnetic . . . 1999 (Year: 1999).*
(Continued)

*Primary Examiner* — Michelle M Entezari Hausmann
(74) *Attorney, Agent, or Firm* — Oliff PLC

(57) ABSTRACT

A color conversion section for an imaging device carries out conversion to imaging data imaged by each medical imaging device for eliminating differences in color property of each imaging device, and generates standard color graphic data. To this standard color graphic data, a color conversion section for highlighting a specific tissue carries out color conversion for highlighting a designated specific biotissue, such as a blood vessel, to generate specific tissue highlighted
(Continued)

graphic data. To this specific tissue highlighted graphic data, a color conversion section for a monitor carries out conversion for eliminating differences in color property of each monitor to generate display data. Color monitors display graphics based on this display data.

17 Claims, 15 Drawing Sheets

(51) Int. Cl.
    *A61B 1/05*     (2006.01)
    *G06T 7/00*     (2017.01)
(52) U.S. Cl.
    CPC ............... *A61B 1/042* (2013.01); *A61B 1/05* (2013.01); *G06T 7/0012* (2013.01); *G06T 2207/10024* (2013.01); *G06T 2207/10068* (2013.01)

(56) References Cited

U.S. PATENT DOCUMENTS

| | | | |
|---|---|---|---|
| 2006/0087557 A1 | 4/2006 | Donomae et al. | |
| 2008/0260227 A1* | 10/2008 | Hayashi | A61B 8/06 600/443 |
| 2009/0023991 A1 | 1/2009 | Gono et al. | |
| 2014/0015946 A1 | 1/2014 | Yanagidate | |
| 2017/0323443 A1* | 11/2017 | Dhruwdas | G06T 11/006 |
| 2017/0340273 A1 | 11/2017 | Morita | |
| 2018/0247153 A1* | 8/2018 | Ganapati | G06F 18/285 |
| 2018/0296075 A1* | 10/2018 | Meglan | A61B 1/00048 |
| 2019/0069957 A1* | 3/2019 | Barral | A61B 34/20 |
| 2019/0197712 A1* | 6/2019 | Talbert | A61B 1/00066 |
| 2019/0301941 A1* | 10/2019 | Kawabata | G01J 3/52 |
| 2019/0343369 A1* | 11/2019 | Makino | A61B 1/000096 |
| 2020/0029891 A1* | 1/2020 | Swisher | A61B 5/489 |
| 2020/0219237 A1* | 7/2020 | Ramsay | G06T 5/94 |
| 2020/0258233 A1* | 8/2020 | Kruecker | G06T 7/73 |

FOREIGN PATENT DOCUMENTS

| | | |
|---|---|---|
| JP | H01-138876 A | 5/1989 |
| JP | 2000-237206 A | 9/2000 |
| JP | 2005-046200 A | 2/2005 |
| JP | 2006-142002 A | 6/2006 |
| JP | 2006-311352 A | 11/2006 |
| JP | 2008-093225 A | 4/2008 |
| JP | 2011-136132 A | 7/2011 |
| JP | 2015-116425 A | 6/2015 |

OTHER PUBLICATIONS

Apr. 7, 2020 International Search Report issued in International Patent Application No. PCT/JP2020/005770.
Badano, Aldo et al., "Consistency and Standardization of Color in Medical Imaging: A Consensus Report," J. Digit Imaging, 2015, pp. 41-52, vol. 28.

* cited by examiner

71: Three primary color chart

72: Multicolor chart

73: Wide gamut color chart

Individual conversion data (LUT)

| Before conversion | | | After conversion | | |
|---|---|---|---|---|---|
| Rold | Gold | Bold | Rnew | Gnew | Bnew |
| 0 | 0 | 0 | 0 | 0 | 0 |
| 0 | 0 | 1 | 0 | 0 | 1 |
| 0 | 0 | 2 | 0 | 1 | 3 |
| ⋮ | ⋮ | ⋮ | ⋮ | ⋮ | ⋮ |
| l | m | n | l′ | m′ | n′ |
| ⋮ | ⋮ | ⋮ | ⋮ | ⋮ | ⋮ |
| 255 | 255 | 253 | 254 | 253 | 251 |
| 255 | 255 | 254 | 254 | 254 | 252 |
| 255 | 255 | 255 | 255 | 255 | 255 |

FIG. 6A

Individual conversion data (mathematical function)

$Rnew = f1(Rold, Gold, Bold)$
$Gnew = f2(Rold, Gold, Bold)$
$Bnew = f3(Rold, Gold, Bold)$

FIG. 6B

Color distribution of multicolor chart 72 itself in FIG. 5B
(measurement under D65 light source)

Color distribution of multicolor chart 72 in FIG. 5B
on monitor screen in conventional system
(imaged under D65 light source)

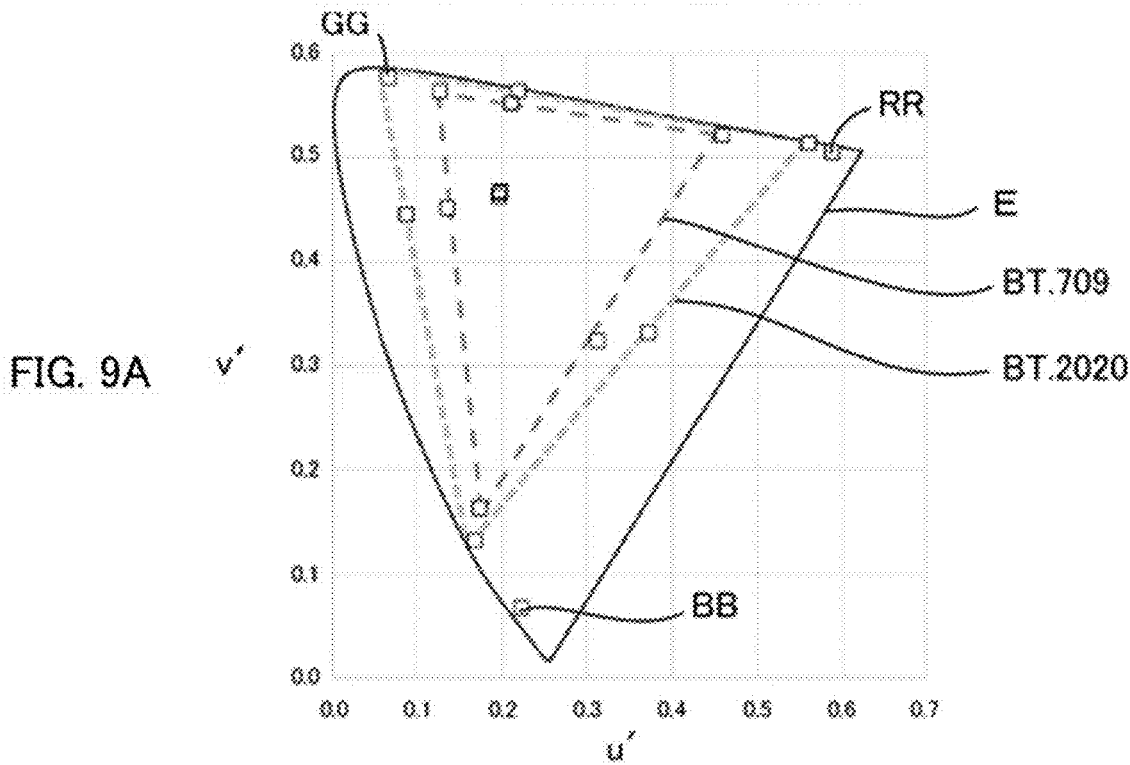
FIG. 9A — Color distribution of wide gamut color chart 73 itself in FIG. 5C (measurement under D65 light source)
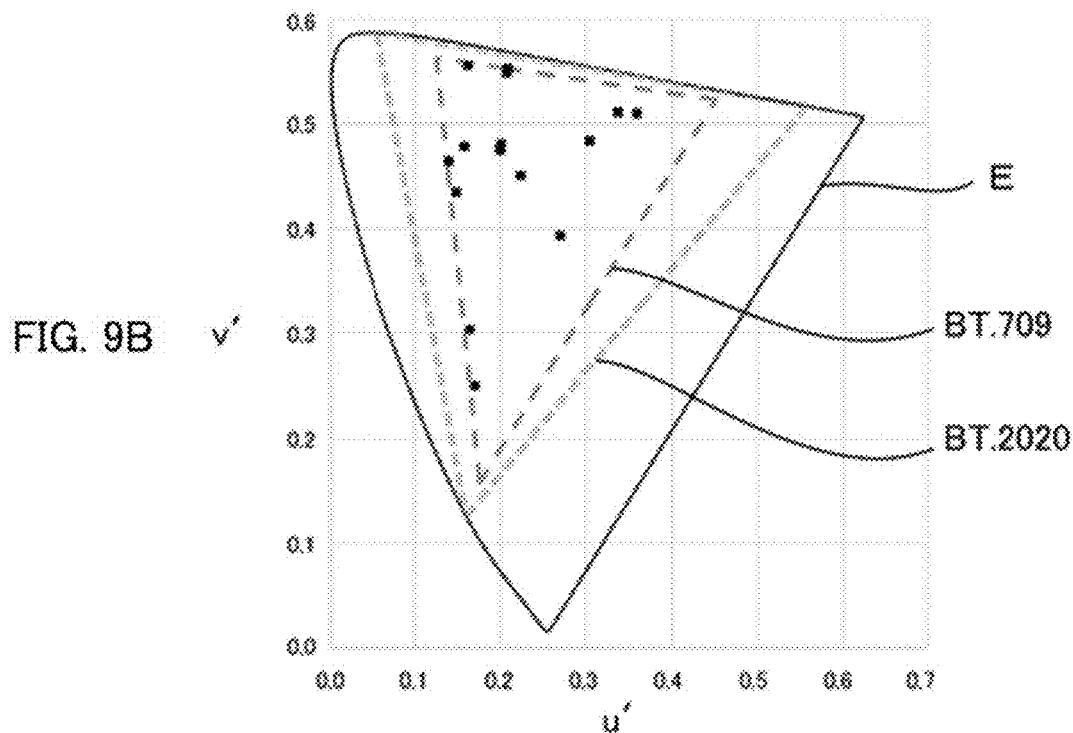
FIG. 9B — Color distribution of wide gamut color chart 73 FIG. 5C on monitor screen in conventional system (imaged under D65 light source)

◎ $\dfrac{\text{Area}(M)}{\text{Area}(BT.709)} = 63\%$ (Using only 63% of the color gamut of a high-definition monitor)

◎ $\dfrac{\text{Area}(M)}{\text{Area}(BT.2020)} = 37\%$ (Using only 37% of the color gamut of a 4K8K monitor)

COLOR CORRECTION DEVICE FOR MEDICAL APPARATUS

TECHNICAL FIELD

The present invention relates to a color correction device for a medical apparatus. Particularly, relating to a color correction device configured to carry out a color correction, appropriate for a display on a color monitor, to graphic data obtained by imaging with a medical imaging device, and whose subject is a group of biotissues.

BACKGROUND ART

A medical graphic display system that takes an image of the periphery of an affected area of a patient during a surgery, and displays the image on a monitor screen, is used in many medical sites. For example, in a typical laparotomy surgery, the condition of the surgery may be confirmed on a monitor by using a medical graphic display system that takes the image of the laparotomy area with a camera located in the surgery room and displays thereof on the monitor. Meanwhile, in laparoscopic surgery, the use of the medical graphic display system is indispensable since an endoscope camera must be inserted into the patient's abdominal cavity without laparotomy, and the procedure must be carried out while viewing the image displayed on the monitor. Also, not only the surgery but also when examining or diagnosing a sample tissue cut out from a human body, a medical graphic display system that takes the image thereof and displays on a monitor, may be used.

For example, below described Patent Literature 1 discloses a medical graphic display system for inserting an endoscope camera into a patient's body cavity and displaying the graphic of the inside of the body cavity on a monitor, and Patent Literature 2 discloses a system for supporting a remote surgery by transmitting a graphic taken with an endoscope camera via a public line and displaying thereof on a remotely located monitor. Meanwhile, a system that carries out some kind of graphic processing to the image taken during a surgery and displays on a monitor, has been proposed. For example, Patent Literature 3 discloses a surgery system that display more appropriate image on a monitor by processing the graphic taken during a surgery so as the graphic matches an observation direction of a practitioner. Also, Patent Literature 4 discloses a medical graphic display system capable of generating three-dimensional volume data from the imaging data of the affected area of a patient under surgery, and displaying the CT graphic during surgery on a monitor based on the generated data.

CITATION LIST

Patent Literatures

Patent Literature 1: Japanese Patent Application Laid-Open (JP-A) No. 2015-116425
Patent Literature 2: JP-A No. 2000-237206
Patent Literature 3: JP-A No. 2005-046200
Patent Literature 4: JP-A No. 2011-136132

SUMMARY OF DISCLOSURE

Technical Problem

Many of the above described medical graphic display system are provided by a single provider, as a set of products including whole system from a camera to a monitor. However, for each provider, the type of the camera and the monitor used varies, and the adjustment criteria for the property thereof also varies. Under such circumstances, the medical graphic display systems currently provided by a plurality of providers have mutually differing color property. Therefore, even if an image of a completely identical subject is imaged under a completely identical illumination and displayed on a color monitor, the color tone of the subject displayed on the monitor will differ for each individual medical graphic display system.

Generally, cameras and monitors have peculiar color property for each apparatus. For example, when an image of a completely identical subject is taken with a plurality of cameras under a completely identical illumination, the resulting graphic data (usually data including an aggregate of pixels with values of three primary colors R, G, and B) will differ for each camera. This is because the color property of the cameras are different from each other. Similarly, when images are displayed by giving completely identical graphic data to a plurality of color monitors, the color reproducibility differs for each monitor. This is because the color property of the color monitors are different from each other. Under such circumstances, the color reproducibility of the medical graphic display system provided by the individual providers is different from each other. This is a major problem for the practitioner to make various diagnoses based on the graphic on the color monitor.

In the future, it is anticipated that the widespread use of such a medical graphic display system will lead to the provision of various medical imaging devices (such as surgical camera, endoscope camera, and microscope camera) and monitors from a large number of providers, and will increase the number of cases of constituting a single medical graphic display system by combining various apparatuses provided by different providers. This further increases the variation in color reproducibility for each individual system, which is detrimental to the practitioner in making a correct diagnosis.

Also, in some surgeries, there are quite a few cases where only a specific biotissue is desired to be examined in detail. As described above, Patent Literature 3 discloses a technique of displaying a graphic on a monitor that matches the observation direction of the practitioner, by processing the taken graphic, and Patent Literature 4 discloses a technique of displaying the CT graphic on a monitor, by generating three-dimensional volume data based on the taken graphic. However, these techniques do not allow graphic display with visibility that is suitable for the examination of a specific biotissue.

The present invention provides a new technique for solving these problems. The first object of the present invention is to eliminate differences in color property among apparatuses and to enable graphic display with a uniform color tone, even when a medical graphic display system is constituted by combining apparatuses having various color property. The second object of the present invention is to enable a graphic display with visibility that is suitable for the examination of a specific biotissue, when utilizing a medical graphic display system.

Solution to Problem (1) The first aspect of the present invention is a color correction device for a medical apparatus configured to carry out a color correction, appropriate for a display on a color monitor, to graphic data obtained by imaging with a medical imaging device, the color correction device for a medical apparatus comprising:

an individual conversion data storage section for an imaging device configured to store individual conversion data for converting a color property of imaging data imaged by a specific medical imaging device into a standard color property, in consideration of a peculiar color property of the medical imaging device, a conversion data storage section for highlighting a specific tissue configured to store conversion data for highlighting a specific tissue for carrying out color conversion highlighting a specific biotissue, an individual conversion data storage section for a monitor configured to store individual conversion data for carrying out color conversion such that a graphic having a standard color property is displayed on a specific color monitor, in consideration of a peculiar color property of the color monitor, a color conversion section for an imaging device configured to generate standard color graphic data by carrying out color conversion, to the imaging data input from the specific medical imaging device, using individual conversion data for the specific medical imaging device stored in the individual conversion data storage section for an imaging device, a highlighting tissue designation section configured to receive a designation input designating a specific biotissue to be highlighted, a color conversion section for highlighting a specific tissue configured to generate specific tissue highlighted graphic data by carrying out color conversion, to the standard color graphic data, using conversion data for highlighting specific tissue for carrying out color conversion for highlighting a specific biotissue designated by the designation input stored in the conversion data storage section for highlighting a specific tissue, and a color conversion section for a monitor configured to generate display data by carrying out color conversion, to the specific tissue highlighted graphic data, using the individual conversion data for the specific color monitor stored in the individual conversion data storage section for a monitor, and to output the generated display data to the specific color monitor.

(2) In the second aspect of the present invention, in the color correction device for a medical apparatus according to the first aspect described above, as the individual conversion data stored in the individual conversion data storage section for an imaging device, conversion data capable of converting a color to a color that covers a wide color gamut of a specification specified in international specification BT.2020 for ultra-high-definition television is used.

(3) In the third aspect of the present invention, in the color correction device for a medical apparatus according to the first or second aspect described above, as the individual conversion data stored in the individual conversion data storage section for an imaging device, conversion data using a color property of transmitted light of a predetermined color chart, employing light from D65 light source specified by Commission Internationale de l'eclairage as a background light, as a standard color property is used.

(4) In the fourth aspect of the present invention, in the color correction device for a medical apparatus according to any one of the first to third aspects described above, as the individual conversion data stored in the individual conversion data storage section for an imaging device, conversion data for converting three primary color components R-old, G-old, and B-old of the imaging data into three primary color components R-new, G-new, and B-new of the standard color graphic data is used.

(5) In the fifth aspect of the present invention, in the color correction device for a medical apparatus according to any one of the first to fourth aspects described above, the individual conversion data for a plurality of I medical imaging devices are stored respectively in the individual conversion data storage section for an imaging device, and to the imaging data input from an i-th ($1 \leq i \leq I$) medical imaging device, the color conversion section for an imaging device carries out color conversion using an i-th individual conversion data so as to generate a standard color graphic data.

(6) In the sixth aspect of the present invention, in the color correction device for a medical apparatus according to any one of the first to fifth aspects described above, the color conversion section for an imaging device inputs the imaging data imaged under a shadowless lamp or an endoscope light source, and generates a standard color graphic data by carrying out a color conversion thereto.

(7) In the seventh aspect of the present invention, in the color correction device for a medical apparatus according to any one of the first to sixth aspects described above, the individual conversion data stored in the individual conversion data storage section for an imaging device include a lookup table configured to convert a combination of each color component constituting the imaging data into a combination of each color component constituting standard color graphic data.

(8) In the eighth aspect of the present invention, in the color correction device for a medical apparatus according to any one of the first to sixth aspects described above, the individual conversion data stored in the individual conversion data storage section for an imaging device include a mathematical function configured to calculate a combination of each color component constituting standard color graphic data, by giving a combination of each color component constituting the imaging data, as a variable value.

(9) In the ninth aspect of the present invention, in the color correction device for a medical apparatus according to any one of the first to eighth aspects described above, the conversion data for highlighting a specific tissue for a plurality of J types of biotissues are stored respectively in the conversion data storage section for highlighting a specific tissue, and when the color conversion section for highlighting a specific tissue receives a designation input designating a j-th ($1 \leq j \leq J$) biotissue from the highlighting tissue designation section, the color conversion is carried out using a j-th conversion data for highlighting a specific tissue so as to generate specific tissue highlighted graphic data.

(10) In the tenth aspect of the present invention, in the color correction device for a medical apparatus according to the ninth aspect described above, the highlighting tissue designation section has a function of receiving designation input designating a plurality of H types ($H \leq J$) of biotissues in an overlapping manner, and when the color conversion section for highlighting a specific tissue receives a designation input designating a plurality of H types of biotissues from the highlighting tissue designation section, the color conversion using a plurality of H types of conversion data for highlighting a specific tissue corresponding to the plurality of H types of biotissues is carried out in an overlapping manner so as to generate the specific tissue highlighted graphic data.

(11) In the eleventh aspect of the present invention, in the color correction device for a medical apparatus according to any one of the first to tenth aspects described above, the highlighting tissue designation section has a function of receiving an empty designation input indicating that none of the biotissue is designated, and when the color conversion section for highlighting a specific tissue receives the empty designation input from the highlighting tissue designation section, the standard color graphic data is output as they are, as the specific tissue highlighted graphic data, without carrying out a color conversion.

(12) In the twelfth aspect of the present invention, in the color correction device for a medical apparatus according to any one of the first to eleventh aspects described above, as the conversion data for highlighting a specific tissue stored in the conversion data storage section for highlighting a specific tissue, data for carrying out a specific color correction, to a color included in a localized color region peculiar to a specific biotissue, in a predetermined color space, is used.

(13) In the thirteenth aspect of the present invention, in the color correction device for a medical apparatus according to the twelfth aspect described above, as the conversion data for highlighting a specific tissue stored in the conversion data storage section for highlighting a specific tissue, data for carrying out color correction that increases or decreases an abscissa value or an ordinate value, or both, with respect to a color included in a localized color region peculiar to a specific biotissue, in a predetermined two-dimensional chromaticity diagram, is used.

(14) In the fourteenth aspect of the present invention, in the color correction device for a medical apparatus according to the thirteenth aspect described above, as the conversion data for highlighting a specific tissue stored in the conversion data storage section for highlighting a specific tissue, data for carrying out color correction that increases or decreases u' value or v' value, or both, with respect to a color included in a localized color region peculiar to a specific biotissue, in u'v' chromaticity diagram, is used.

(15) In the fifteenth aspect of the present invention, in the color correction device for a medical apparatus according to the fourteenth aspect described above, the highlighting tissue designation section has a function of receiving designation input designating "blood vessel" as a specific biotissue to be a subject of a highlighted display, and as the conversion data for highlighting a specific tissue for carrying out color conversion highlighting "blood vessel", the conversion data for carrying out color correction that increases u' values with respect to a color included in localized color region peculiar to the blood vessel, in u'v' chromaticity diagram are stored in the conversion data storage section for highlighting a specific tissue.

(16) In the sixteenth aspect of the present invention, in the color correction device for a medical apparatus according to the fourteenth or fifteenth aspect described above, the highlighting tissue designation section has a function of receiving designation input designating "fat" as a specific biotissue to be a subject of a highlighted display, and as the conversion data for highlighting a specific tissue for carrying out color conversion highlighting "fat", the conversion data for carrying out color correction that decreases u' value as well as increases v' value with respect to a color included in localized color region peculiar to the fat, in u'v' chromaticity diagram are stored in the conversion data storage section for highlighting a specific tissue.

(17) In the seventeenth aspect of the present invention, in the color correction device for a medical apparatus according to any one of the fourteenth to sixteenth aspects described above, the highlighting tissue designation section has a function of receiving designation input designating "surface layer" as a specific biotissue to be a subject of a highlighted display, and as the conversion data for highlighting a specific tissue for carrying out color conversion highlighting "surface layer", the conversion data for carrying out color correction that increases u' value as well as decreases v' value with respect to a color included in localized color region peculiar to the surface layer, in u'v' chromaticity diagram are stored in the conversion data storage section for highlighting a specific tissue.

(18) In the eighteenth aspect of the present invention, in the color correction device for a medical apparatus according to any one of the first to seventeenth aspects described above, as the individual conversion data stored in the individual conversion data storage section for a monitor, conversion data capable of converting a color to a color that covers a wide color gamut of a specification specified in international specification BT.2020 for ultra-high-definition television is used.

(19) In the nineteenth aspect of the present invention, in the color correction device for a medical apparatus according to any one of the first to eighteenth aspects described above, the individual conversion data for a plurality of K color monitors are stored respectively in the individual conversion data storage section for a monitor, and when the color conversion section for a monitor generates display data output to a k-th ($1 \leq k \leq K$) color monitor, color conversion using a k-th individual conversion data is carried out.

(20) In the twentieth aspect of the present invention, in the color correction device for a medical apparatus according to any one of the first to nineteenth aspects described above, the individual conversion data stored in the individual conversion data storage section for a monitor include a lookup table configured to convert a combination of each color component constituting the specific tissue highlighted graphic data into a combination of each color component constituting display data.

(21) In the twenty-first aspect of the present invention, in the color correction device for a medical apparatus according to any one of the first to nineteenth aspects described above, the individual conversion data stored in the individual conversion data storage section for a monitor include a mathematical function configured to calculate a combination of each color component constituting display data, by giving a combination of each color component constituting the specific tissue highlighted graphic data, as a variable value.

(22) The twenty-second aspect of the present invention is a color correction device for a medical apparatus configured to carry out a color correction highlighting a specific biotissue, to graphic data whose subject is a group of biotissues, the color correction device for a medical apparatus comprising:

a conversion data storage section for highlighting a specific tissue configured to store conversion data for highlighting a specific tissue for carrying out color conversion highlighting a specific biotissue, a highlighting tissue designation section configured to receive a designation input designating a specific biotissue to be a subject of a highlighted display, and a color conversion section for highlighting a specific tissue configured to generate specific tissue highlighted graphic data by carrying out color conversion, to graphic data obtained based on an image imaged by a medical imaging device, using conversion data for highlighting specific tissue for carrying out color conversion for highlighting a specific biotissue designated by the designation input stored in the conversion data storage section for highlighting specific tissue.

(23) In the twenty-third aspect of the present invention, in the color correction device for a medical apparatus according to the twenty-second aspect described above, as the conversion data for highlighting a specific tissue stored in the conversion data storage section for highlighting a specific tissue, data for carrying out a specific color correction, to a color included in a specific localized color region peculiar to a specific biotissue, in a predetermined color space, is used.

(24) In the twenty-fourth aspect of the present invention, in the color correction device for a medical apparatus according to the twenty-third aspect described above, as the conversion data for highlighting a specific tissue stored in the conversion data storage section for highlighting a specific tissue, data for carrying out color correction that increases or decreases an abscissa value or an ordinate value, or both, with respect to a color included in a localized color region peculiar to a specific biotissue, in a predetermined two-dimensional chromaticity diagram, is used.

(25) In the twenty-fifth aspect of the present invention, in the color correction device for a medical apparatus according to the twenty-fourth aspect described above, as the conversion data for highlighting a specific tissue stored in the conversion data storage section for highlighting a specific tissue, data for carrying out color correction that increases or decreases u' value or v' value, or both, with respect to a color included in a localized color region peculiar to a specific biotissue, in u'v' chromaticity diagram, is used.

(26) In the twenty-sixth aspect of the present invention, in the color correction device for a medical apparatus according to the twenty-fifth aspect described above, the highlighting tissue designation section has a function of receiving designation input designating "blood vessel" as a specific biotissue to be a subject of a highlighted display, and as the conversion data for highlighting a specific tissue for carrying out color conversion highlighting "blood vessel", the conversion data for carrying out color correction that increases u' values with respect to a color included in localized color region peculiar to the blood vessel, in u'v' chromaticity diagram are stored in the conversion data storage section for highlighting a specific tissue.

(27) In the twenty-seventh aspect of the present invention, in the color correction device for a medical apparatus according to the twenty-fifth or twenty-sixth aspect described above, the highlighting tissue designation section has a function of receiving designation input designating "fat" as a specific biotissue to be a subject of a highlighted display, and as the conversion data for highlighting a specific tissue for carrying out color conversion highlighting "fat", the conversion data for carrying out color correction that decreases u' value as well as increases v' value with respect to a color included in localized color region peculiar to the fat, in u'v' chromaticity diagram are stored in the conversion data storage section for highlighting a specific tissue.

(28) In the twenty-eighth aspect of the present invention, in the color correction device for a medical apparatus according to any one of the twenty-fifth to twenty-seventh aspects described above, the highlighting tissue designation section has a function of receiving designation input designating "surface layer" as a specific biotissue to be a subject of a highlighted display, and as the conversion data for highlighting a specific tissue for carrying out color conversion highlighting "surface layer", the conversion data for carrying out color correction that increases u' value as well as decreases v' value with respect to a color included in localized color region peculiar to the surface layer, in u'v' chromaticity diagram are stored in the conversion data storage section for highlighting a specific tissue.

(29) In the twenty-ninth aspect of the present invention, a medical graphic display system is constituted by adding at least one medical imaging device configured to give imaging data to the color correction device for a medical apparatus, and at least one color monitor configured to display a graphic based on display data output from the color correction device for a medical apparatus, to the color correction device for a medical apparatus according to any one of the first to twenty-first aspects described above.

(30) In the thirtieth aspect of the present invention, a program makes a computer to function as the color correction device for a medical apparatus according to any one of the first to twenty-eighth aspects described above.

Advantageous Effects of Disclosure

The color correction device for a medical apparatus according to the first to twenty-first aspects of the present invention is a device incorporated and used in a medical graphic display system including a medical imaging device and a color monitor. In this color correction device, the difference in color property of individual medical imaging device is eliminated by a color conversion section for an imaging device, and the difference in color property of individual color monitors is eliminated by a color conversion section for a monitor. Therefore, the first object of the present invention "to eliminate differences in color property among apparatuses and to enable graphic display with a uniform color tone, even when a medical graphic display system is constituted by combining apparatuses having various color property" is achieved. Further, since this color correction device generates a standard color graphic data by conversion by the color conversion section for an imaging device, and a color conversion highlighting a specific biotissue is carried out to this standard color graphic data, the second object of the present invention "to enable a graphic display with visibility that is suitable for the examination of a specific biotissue" is also achieved.

Meanwhile, the color correction device for a medical apparatus according to the twenty-second to twenty-eighth aspects is also a device incorporated and used in a medical graphic display system including a medical imaging device and a color monitor. In this color correction device, since a color conversion highlighting a specific biotissue is carried out, to a graphic data obtained based on an image imaged by a medical imaging device, the second object of the present invention "to enable a graphic display with visibility that is suitable for the examination of a specific biotissue" is achieved.

BRIEF DESCRIPTION OF DRAWINGS

FIGS. 6A and 6B are diagrams illustrating a specific example of individual conversion data to be stored in individual conversion data storage section for an imaging device 110 and individual conversion data to be stored in individual conversion data storage section for a monitor 130 illustrated in FIG. 3.

FIGS. 9A and 9B are u'v' chromaticity diagrams illustrating the color distribution obtained by the measurement procedure illustrated in FIGS. 7A and 7B, to wide gamut color chart 73 illustrated in FIG. 5C.

DESCRIPTION OF EMBODIMENTS

The present invention is hereinafter explained based on the embodiments illustrated in the figures.

<<< § 1. Common Conventional Medical Graphic Display System>>>

Figure 1:
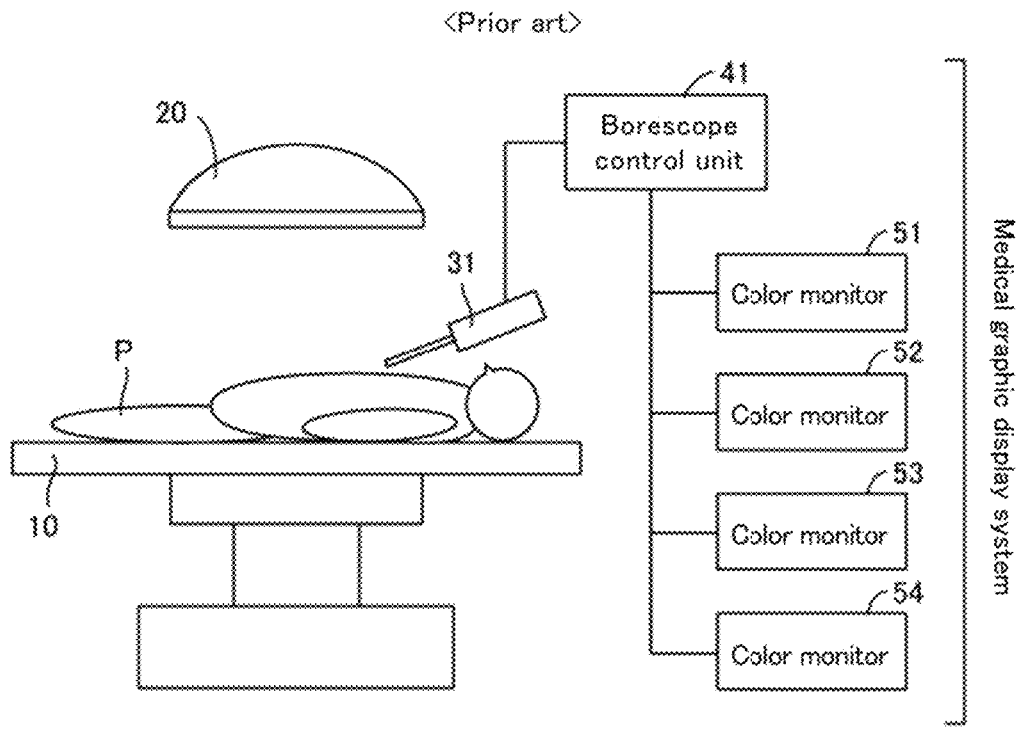
FIG. 1 is a block diagram illustrating the condition of a surgery room provided with a common conventional medical graphic display system.

First, a common conventional medical graphic display system will be briefly described. FIG. 1 is a block diagram illustrating the condition of a surgery room provided with a common conventional medical graphic display system. As illustrated in the figure, the surgery room is provided with surgical table 10, and subject (patient) P lies thereon. Shadowless lamp 20 is provided above surgical table 10 to illuminate the affected area of subject P. The illustrated example is an example wherein a laparoscopic surgery is carried out to subject P; during surgery, an opening having a diameter of around 10 mm is formed in the abdomen of subject P; and the leading end of endoscope camera 31 is inserted into the abdominal cavity of subject P.

Endoscope camera 31 is connected to endoscope control unit 41 by a cable. Endoscope control unit 41 is a device configured to control endoscope camera 31, and has functions such as supplying power to endoscope camera 31, capturing imaging data from endoscope camera 31, ON/OFF of an endoscope light source attached to endoscope camera 31, and recording of imaging data. Although only one endoscope camera 31 is illustrated in the figure, a plurality of endoscope cameras may be used as required.

In the illustrated example, four color monitors 51-54 are connected to endoscope control unit 41, and the graphic taken by endoscope camera 31 is transmitted to each color monitor 51-54 via endoscope control unit 41, and displayed on each screen. The practitioner carries out a laparoscopic surgery while looking at the graphic on the screen (surgery instrument is not illustrated in the figure). Color monitors 51-54 need not necessarily be provided in the surgery room, and may be partially or entirely provided in another room (such as a conference room). In the systems disclosed in Patent Literature 2 above, the monitor is located at a remote location and surgery is carried out by remote control.

In the example illustrated in FIG. 1, the system including endoscope camera 31, endoscope control unit 41, and color monitors 51 to 54 constitutes the medical graphic display system. Certainly, for a typical laparotomy surgery, such a medical graphic display system is introduced as required. In a laparotomy surgery, a conventional camera that takes an image of the affected area from above is usually used instead of endoscope camera 31. In a special laparotomy surgery, however, a endoscope camera may be used in combination. In laparotomy surgery, the practitioner usually carries out the procedure while observing the affected area with the naked eye. Therefore, display graphic on the monitor is used as information presented to the practitioner assistant or other people involved.

Figure 2:
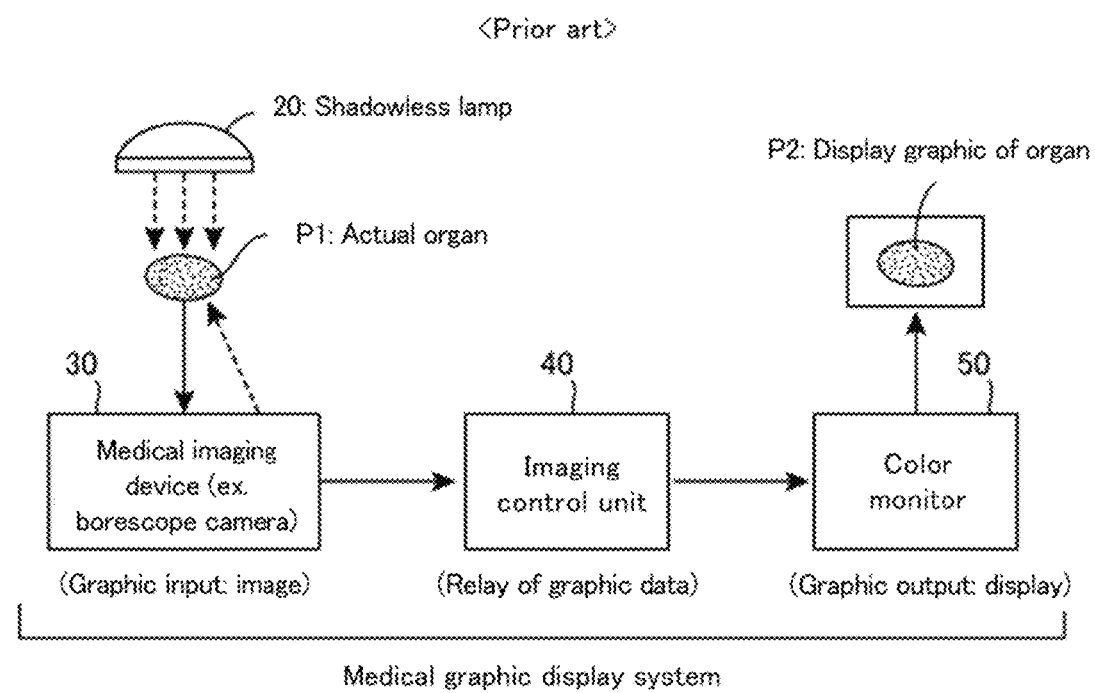
FIG. 2 is a block diagram illustrating a flow of graphic data in a common conventional medical graphic display system.

FIG. 2 is a block diagram illustrating a flow of graphic data in a common conventional medical graphic display system. FIG. 2 illustrates an example wherein graphic of the actual organ P1 that is the affected part of subject P is imaged with medical imaging device 30, the obtained imaging data is transmitted to color monitor 50 via imaging control unit 40, and display graphic P2 of the organ is displayed on the screen. In a laparoscopic surgery as illustrated in FIG. 1, endoscope camera 31 is used as medical imaging device 30, and endoscope control unit 41 is used as imaging control unit 40. Above the subject P, shadowless lamp 20 is provided, and subject P is illuminated with the light from this shadowless lamp 20 (in FIG. 2, the dashed arrow from shadowless lamp 20 to actual organ P1 indicates such illumination light). However, in the laparoscopic surgery, since the illumination light from shadowless lamp 20 does not reach actual organ P1 as a subject, the illumination light is received from a endoscope light source (endoscope camera collateral light source) attached to the endoscope camera (in FIG. 2, a broken arrow from medical imaging device 30 to actual organ P1 indicates the illumination light from this endoscope light source).

Eventually, in the example illustrated in FIG. 2, the system including medical imaging device 30, imaging control unit 40, and color monitor 50 constitutes the medical graphic display system. Here, medical imaging device 30 is a component configured to input graphic by imaging actual organ P1, imaging control unit 40 is a component configured to relay graphic data obtained by this graphic input, and color monitor 50 is a component configured to output graphic by displaying display graphic P2 of organ on the screen based on a given graphic data.

As described above, medical imaging device 30 and color monitor 50 have a peculiar color property for each apparatus. For this reason, there is usually a difference between the color tone of display graphic P2 of organ displayed on the screen of color monitor 50 and the color tone of actual organ P1 (the color tone under illumination of shadowless lamp 20 or endoscope light source). Also, the difference in color tone differs according to a apparatus actually used as medical imaging device 30 or a apparatus actually used as color monitor 50. For this reason, when a plurality of types of cameras are used as medical imaging device 30 or a plurality of types of apparatuses are used as color monitor 50, the color tone of display graphic P2 of organ is changed according to the specific aspect such that graphic shot by which camera is displayed by which color monitor.

In the future, it is expected that a large number of endoscope camera having various properties will be developed and provided from various providers, and a large number of color monitors having various properties will be developed and provided from various providers. In this way, when the medical graphic display system is constituted by combining the apparatuses having various color property, the color tone of display graphic P2 of organ also varies. This is a major issue for the practitioner to make various diagnoses based on graphic on color monitor 50.

In the systems described in Patent Literature 3 above, graphic processing is carried out to the taken graphic in the device corresponding to imaging control unit 40, and graphic that matches the observation direction of the practitioner is displayed on color monitor 50. However, the process of resolving the difference in color property of the respective apparatuses is not carried out. In the systems described in Patent Literature 4 above, three-dimensional volumetric data is generated in the device corresponding to imaging control unit 40, and the CT graphic is displayed on the color monitor. However, the process of resolving the difference in color property of the respective apparatuses is not carried out.

As described above, in the conventional medical graphic display system, when a medical graphic display system is constituted by combining apparatuses having various color property, there is a problem that the color tone of graphic displayed on the color monitor is not unified due to the differences in color property between the apparatuses. In view of the above problems, the first object of the present invention is to eliminate differences in color property among apparatuses and to enable graphic display with a uniform color tone, even when a medical graphic display system is constituted by combining apparatuses having various color property.

Also, from the standpoint of the practitioner who actually carries out surgery, it may be desired to observe only a specific biotissue in detail. However, the conventional medical graphic display system illustrated in FIGS. 1 and 2 cannot satisfy such a requirement. For example, when blood vessel of an organ is to be treated, the practitioner would like to proceed with surgery while closely monitoring the blood vessel portion. However, in the conventional medical graphic display system, since the blood vessel portion is displayed on the color monitor in a reddish color as a whole, it is difficult to find out a subtle difference in color tone or shade of the blood vessel portion from the displayed graphic on the color monitor. In view of the above problems, the second object of the present invention is to enable a graphic display with visibility that is suitable for the examination of a specific biotissue.

Accordingly, in § 2 and subsequent, a color correction device for a medical apparatus according to the present invention capable of achieving the above two objects will be described in detail.

<<< § 2. Medical Graphic Display System According to Present Invention>>>

Here, the basic configuration and basic functions of the medical graphic display system according to the present invention and the color correction device for a medical apparatus incorporated and used in the system will be described.

<2.0 Basic Configuration of Medical Graphic Display System>

Figure 3:
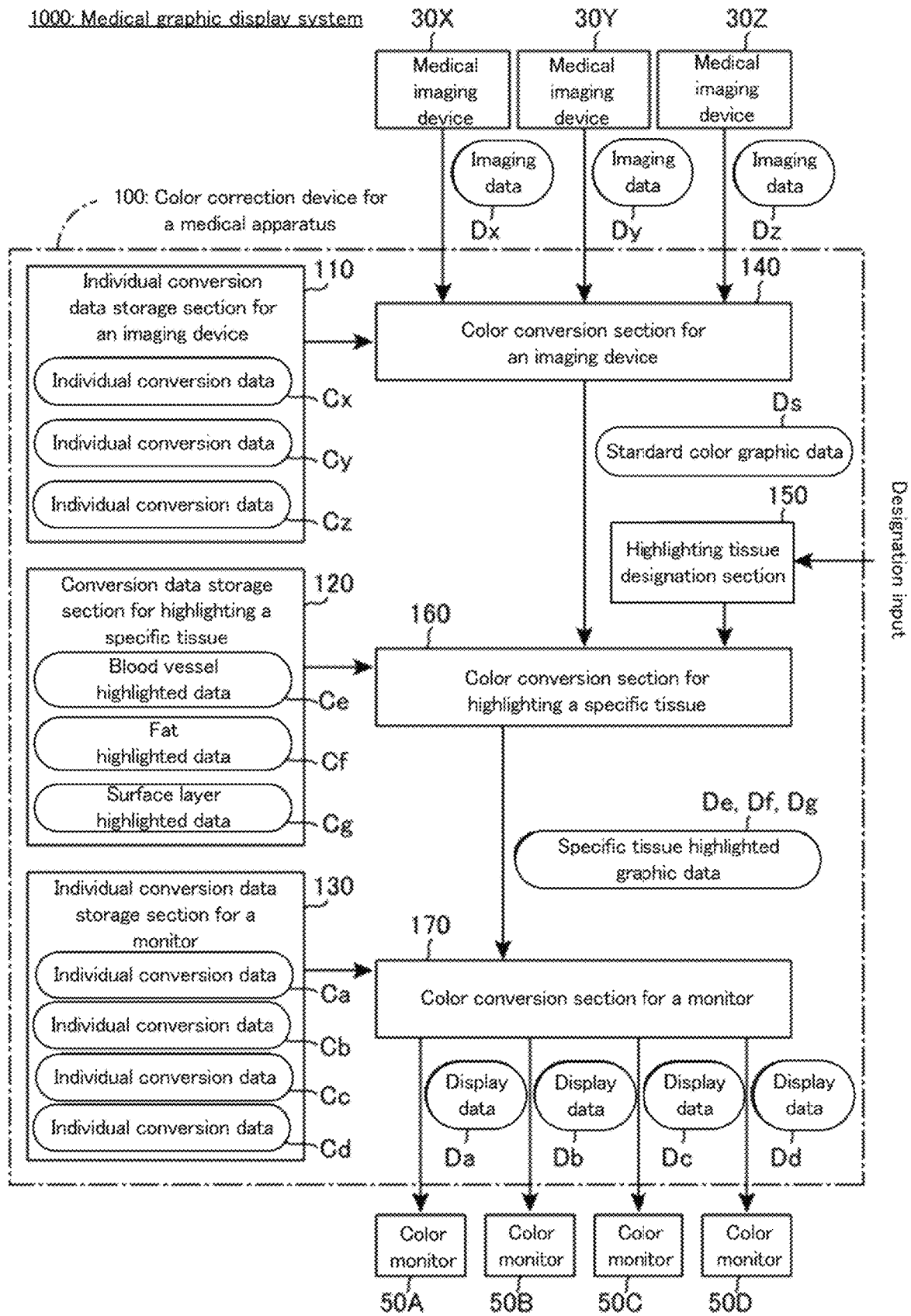
FIG. 3 is a block diagram illustrating a basic configuration of medical graphic display system 1000 including color correction device for a medical apparatus 100 according to the present invention.

FIG. 3 is a block diagram illustrating a basic configuration of medical graphic display system 1000 including color correction device for a medical apparatus 100 according to the present invention. Medical graphic display system 1000 illustrated here comprises three medical imaging devices 30X-30Z, four color monitors 50A-50D, and one color correction device for a medical apparatus 100. Comparing medical graphic display system 1000 illustrated in FIG. 3 with the conventional medical graphic display system illustrated in FIG. 2, medical imaging devices 30X-30Z correspond to medical imaging device 30, color monitors 50A-50D correspond to color monitor 50, and color correction device for a medical apparatus 100 corresponds to imaging control unit 40. However, while imaging control unit 40 illustrated in FIG. 2 has only a relay function of transmitting imaging data obtained from medical imaging device 30 to color monitor 50 as it is, color correction device for a medical apparatus 100 illustrated in FIG. 3 has a function of carrying out a predetermined color correction process to imaging data Dx-Dz obtained from medical imaging device 30X-30Z to generate each display data Da-Dd suitable for each color monitor 50A-50D.

Medical imaging device 30X-30Z may be any device that takes graphic for medical-use. Specifically, for example, it may be an endoscope camera used in a laparoscopic surgery, and it may be a usual video camera located in a surgery room. Certainly, the graphic data taken by medical imaging devices 30X-30Z may be still image data, and may be moving image data. Also, medical graphic display system 1000 illustrated here is not limited to the use for surgery, and may be used for the purpose of taking image of a sample tissue cut out from a human body, displaying the sample tissue on a color monitor, and examining and diagnosing. When using for such a use, for example, a microscope camera may be used as a medical imaging device.

Meanwhile, color monitors 50A-50D may be any device as long as it has a function of displaying a color graphic. Generally, a color display used by connecting to a computer may be used as color monitors 50A-50D. As mentioned in § 1, the location of the respective color monitor 50A-50D is also optional.

Incidentally, for convenience of explanation, an example of medical graphic display system 1000 configured by connecting three medical imaging devices 30X-30Z and four color monitors 50A-50D to color correction device for a medical apparatus 100. However, the number of medical imaging devices and the number of color monitors may be arbitrarily selected. To configure medical graphic display system 1000 according to the present invention, it is sufficient to connect at least one medical imaging device 30 and at least one color monitor 50 to color correction device for a medical apparatus 100.

As illustrated by surrounding with a chain line in the figure, color correction device for a medical apparatus 100 illustrated in FIG. 3 includes individual conversion data storage section for an imaging device 110, conversion data storage section for highlighting a specific tissue 120, individual conversion data storage section for a monitor 130, color conversion section for an imaging device 140, highlighting tissue designation section 150, color conversion section for highlighting a specific tissue 160, and color conversion section for a monitor 170. In practice, each of these components may be implemented by incorporating a dedicated program into a computer. Therefore, in practical use, color correction device for a medical apparatus 100 illustrated in FIG. 3 is constituted by a computer incorporating a dedicated program, and medical imaging devices 30X-30Z and color monitors 50A-50D are connected to this computer. Incidentally, in FIG. 3, the individual components are represented by rectangular blocks, and the digital data transmitted and received between the rectangular blocks are represented by ellipse blocks.

This color correction device for a medical apparatus 100 has a function of carrying out a color correction, appropriate for a display on color monitors 50A-50D, to graphic data (actually a plurality of graphic data arranged in time series in order to configure a moving image) obtained by imaging with medical imaging device 30X-30Z. In the block diagram in FIG. 3, graphic data (graphic data input to color correction device for a medical apparatus 100) obtained by imaging by each medical imaging device 30X-30Z are respectively referred to as imaging data Dx, Dy, and Dz, and graphic data (graphic data output from color correction device for a medical apparatus 100) given to each color monitor 50A-50D is respectively referred to as display data Da, db, Dc, and Dd. Therefore, color correction device for a medical apparatus 100 carries out predetermined color correction process to input imaging data Dx, Dy, and Dz respectively, and outputs the treated graphic data as display data Da, db, Dc, and Dd.

Such a color correction process is executed as a three-stage conversion process. The first conversion process is a process carried out to the input imaging data Dx, Dy, and Dz, and is executed by color conversion section for an imaging device 140 using individual conversion data Cx, Cy, and Cz stored in individual conversion data storage section for an imaging device 110. The object of the first conversion process is to eliminate the difference of color property between the apparatuses of each medical imaging device 30X, 30Y, and 30Z. Standard color graphic data Ds output from color conversion section for an imaging device 140 will be graphic data with a standard color tint that the difference in color property of each apparatus is eliminated.

The subsequent second conversion process is a process carried out to standard color graphic data Ds output from color conversion section for an imaging device 140, and is carried out by color conversion section for highlighting a specific tissue 160 using conversion data for highlighting a specific tissue stored in conversion data storage section for highlighting a specific tissue 120 (in the illustrated example, blood vessel highlighted data Ce, fat highlighted data Cf, and the surface layer highlighted data Cg). The object of this second conversion process is to carry out a color conversion highlighting a specific biotissue, in order to display a graphic with visibility that is suitable for the examination of the specific biotissue designated by an operator. The specific tissue highlighted graphic data output from color conversion section for highlighting a specific tissue 160 (in the figure, data De, Df, and Dg are illustrated, according to designated biotissue) will be graphic data corresponding to a graphic with visibility that is suitable for the examination of the specific biotissue.

The third conversion process carried out at the last is a process carried out to specific tissue highlighted graphic data De, Df, and Dg output from color conversion section for highlighting a specific tissue 160, and is executed by color conversion section for a monitor 170 using individual conversion data Ca, Cb, Cc, and Cd stored in individual conversion data storage section for a monitor 130. The object of the third conversion process is to eliminate the difference in color property between apparatuses of each color monitor 50A-50D, and each display data Da, db, Dc, and Dd output from color conversion section for a monitor 170 will be graphic data corrected to eliminate the difference in color property between each apparatus.

Incidentally, in FIG. 3, the downwardly directed arrows do not indicate the flow of the individual graphic data itself, but indicate the flow of the conversion process relating to the tint. For example, three downward arrows are indicated for the input stage of color conversion section for an imaging device 140, while only one down arrow is indicated for the output stage. This indicates that the three sets of imaging data Dx, Dy, and Dz on the input side each have a peculiar tint, while standard color graphic data Ds on the output side have a common standard color. In other words, even when an image of an identical subject is taken under an identical condition, the three downward arrows of the input stage indicate that imaging data Dx, Dy, and Dz are data different from each other (data having different tint) due to the peculiar color property of each imaging device, and the one downward arrow of the output stage indicates that the difference in color tint of imaging data Dx, Dy, and Dz is eliminated by the converting process by color conversion section for an imaging device 140, and standard color graphic data Ds having the common tint is obtained.

Color conversion section for highlighting a specific tissue 160 converts the tint of this standard color graphic data Ds according to the specific biotissue to be highlighted, and outputs specific tissue highlighted graphic data (any one of graphic data De, Df, and Dg). Therefore, at the input stage of color conversion section for a monitor 170, specific tissue highlighted graphic data indicated by one single downward arrow are given. The four downward arrows indicated on the output stage of color conversion section for a monitor 170 indicate that the tint of display data Da-Dd given to each color monitor 50A-50D differ according to the peculiar color property of each color monitor 50A-50D. In other words, even when the identical specific tissue highlighted graphic data is given to the input stage of color conversion section for a monitor 170, display data Da-Dd different to each other are obtained on the output stage.

<2.1 Basic Operation Relating First Conversion Process>

Next, the basic functions of the individual components illustrated as rectangular blocks in color correction device for a medical apparatus 100 will be described in order. First, the basic functions of individual conversion data storage section for an imaging device 110 and color conversion section for an imaging device 140 relating to the first conversion process (the process carried out to input imaging data Dx, Dy, and Dz) will be described.

First, individual conversion data storage section for an imaging device 110 is a component configured to store individual conversion data for converting color property of imaging data imaged by a specific medical imaging device into a standard color property, in consideration of a peculiar color property of the medical imaging device. In the example illustrated in FIG. 3, since three medical imaging devices 30X, 30Y, and 30Z are connected to color correction device for a medical apparatus 100, individual conversion data storage section for an imaging device 110 is provided with individual conversion data Cx, Cy, and Cz respectively corresponding to these three medical imaging devices 30X, 30Y, and 30Z. For example, individual conversion data Cx is conversion data for converting color property of imaging data Dx taken by medical imaging device 30X into the standard color property, in consideration of the peculiar color property of medical imaging device 30X. The substance of such conversion data is described in detail in § 3.

Color conversion section for an imaging device 140 is a component configured to generate a standard color graphic data by carrying out color conversion, to the imaging data input from the specific medical imaging device, using individual conversion data for the specific medical imaging device stored in the individual conversion data storage section for an imaging device 110. For example, when imaging data Dx are given from medical imaging device 30X, color conversion section for an imaging device 140 carries out color conversion to the imaging data Dx, using individual conversion data Cx for medical imaging device 30X stored in individual conversion data storage section for an imaging device 110 to generate standard color graphic data Ds.

In the illustrated example, since three medical imaging devices 30X, 30Y, and 30Z are connected to color correction device for a medical apparatus 100, three sets of individual conversion data Cx, Cy, and Cz are prepared in individual conversion data storage section for an imaging device 110. Generally, when the use of a plurality of I medical imaging device is assumed, the individual conversion data for these I medical imaging device may be stored respectively in individual conversion data storage section for an imaging device 110. In this case, color conversion section for an imaging device 140 carries out color conversion to imaging data Di input from the i-th (1≤i≤I) medical imaging device 30i, using the i-th individual conversion data Ci (individual conversion data for the i-th medical imaging device 30i) to generate standard color graphic data Ds.

Thus, standard color graphic data Ds obtained by color conversion process by color conversion section for an imaging device 140 is obtained by converting color property peculiar to each medical imaging device into a standard color property, so that graphic data will have a uniform color tone that differences in color property for each device is eliminated. Therefore, when an image of an identical subject is taken under the identical imaging conditions by three medical imaging devices 30X, 30Y, and 30Z, although the contents of the resulting imaging data Dx, Dy, and Dz will be different from each other, three standard color graphic data (here, referred to as Dsx, Dsy, and Dsz) obtained by color conversion process to these imaging data Dx, Dy, and Dz will be theoretically the identical graphic data. In other words, the tint of the graphic expressed by individual imaging data Dx, Dy, and Dz differ from each other according to color property peculiar to each imaging device, but the tint of graphic expressed by standard color graphic data Dsx, Dsy, and Dsz obtained after color conversion by color conversion section for an imaging device 140 are theoretically identical.

<2.2 Basic Operation Relating Second Conversion Process>

Next, basic functions of conversion data storage section for highlighting a specific tissue 120, highlighting tissue designation section 150, and color conversion section for highlighting a specific tissue 160 relating to the second conversion process (process carried out to standard color graphic data Ds output from color conversion section for an imaging device 140) will be described.

One of the major features of color correction device for a medical apparatus 100 illustrated in FIG. 3 is that imaging data Dx, Dy, and Dz obtained from each medical imaging devices 30X, 30Y, and 30Z are once converted into standard color graphic data Ds by color conversion processing by color conversion section for an imaging device 140 (first conversion process), and this standard color graphic data Ds is subjected to color conversion process by color conversion section for highlighting a specific tissue 160 to generate specific tissue highlighted graphic data De, Df, and Dg highlighting a specific biotissue (second conversion process), and further, color conversion process by color conversion section for a monitor 170 is carried out thereto, to generate display data Da-Dd corresponding to each color monitor 50A-50D (third conversion process). Since the subject of color conversion process by color conversion section for highlighting a specific tissue 160 is standard color graphic data Ds having the standard tint, color property peculiar to each medical imaging device 30X, 30Y, and 30Z is not need to be considered when the color conversion process by color conversion section for highlighting a specific tissue 160 is carried out.

Therefore, conversion data storage section for highlighting a specific tissue 120 may store conversion data for highlighting a specific tissue for carrying out color conversion highlighting a specific biotissue, to standard color graphic data Ds having the standard tint. In the example illustrated in FIG. 3, three conversion data for highlighting a specific tissue are stored in conversion data storage section for highlighting a specific tissue 120. Specifically, three conversion data for highlighting a specific tissue are stored: blood vessel highlighted data Ce for carrying out color conversion highlighting the blood vessel, fat highlighted data Cf for carrying out color conversion highlighting the fat, and surface layer highlighted data Cg for carrying out color conversion highlighting the surface layer (a film constituting a surface layer such as organ). The substance of these conversion data for highlighting a specific tissue Ce, Cf, and Cg and a specific example of "highlighted display" of a specific biotissue are detailed in § 6.

Highlighting tissue designation section 150 is a component configured to receive a designation input designating a specific biotissue to be the subject of a highlighted display. This designation input is made by an operator of color correction device for a medical apparatus 100 (such as a practitioner, if surgery is in progress). For the graphic to be displayed on color monitors 50A-50D, the operator inputs a signal to designate a biotissue to be highlighted. In short, the operator may designate a specific biotissue from the viewpoint of which biotissue should be displayed with a visibility improved graphic, or in other words, which biotissue should be displayed with a graphic suitable for examination. Highlighting tissue designation section 150 is responsible for transmitting the designation input from the operator to color conversion section for highlighting a specific tissue 160.

Color conversion section for highlighting a specific tissue 160 generates specific tissue highlighted graphic data by carrying out color conversion, to standard color graphic data Ds, using conversion data for highlighting specific tissue for carrying out color conversion highlighting a specific biotissue designated by the designation input stored in the conversion data storage section for highlighting a specific tissue 120. For example, when the operator inputs designating "blood vessel" as a specific biotissue to be to be the subject of the highlighted display, a signal that the subject to be highlighted is "blood vessel" is transmitted from highlighting tissue designation section 150 to color conversion section for highlighting a specific tissue 160. Therefore, color conversion section for highlighting a specific tissue 160 selects blood vessel highlighted data Ce among the three sets of conversion data for highlighting a specific tissue stored in conversion data storage section for highlighting a specific tissue 120, carries out color conversion process to standard color graphic data Ds using this blood vessel highlighted data Ce, and outputs specific tissue highlighted graphic data De for the blood vessel, as the processed graphic data. Similarly, when "fat" or "surface layer" is designated as the subject to be highlighted, specific tissue highlighted graphic data Df for fat or specific tissue highlighted graphic data Dg for surface layer is output by color conversion process using fat highlighted data Cf or surface layer highlighted data Cg.

In the example illustrated in the figure, three types of biotissue "blood vessel", "fat" and "surface layer" that may be designated as the subject of highlighted display are prepared; needless to say, various types of biotissue such as "bone", "cartilage" and "muscle", beside the above, may be designated as the subject of the highlighted display. In short, when a plurality of types of biotissue are to be highlighted, conversion data for highlighting specific tissue for a plurality of J biotissues may be stored in conversion data storage section for highlighting a specific tissue 120 respectively, and when color conversion section for highlighting a specific tissue 160 receives a designation input that designates the j-th ($1 \leq j \leq J$) biotissue from highlighting tissue designation section 150, color conversion using the j-th conversion data for highlighting a specific tissue Cj (conversion data for highlighting the j-th biotissue) may be carried out to generate specific tissue highlighted graphic data.

Incidentally, the designation input to highlighting tissue designation section 150 does not necessarily have to be an input designating a single biotissue, and may be an input designating a plurality of biotissues. For example, if the operator wishes to highlight both "blood vessel" and "fat", input may be made to highlighting tissue designation section 150 designating the both. In this case, since a signal that both the "blood vessel" and the "fat" are designated is transmitted from highlighting tissue designation section 150 to color conversion section for highlighting a specific tissue 160, color conversion section for highlighting a specific tissue 160 carries out color conversion using blood vessel highlighted data Ce and color conversion using fat highlighted data Cf in an overlapped manner, to standard color graphic data Ds, and outputs specific tissue highlighted graphic data Def. The display on the color monitor using this specific tissue highlighted graphic data Def is a display wherein both "blood vessel" and "fat" are highlighted.

In short, in order to enable to designate a plurality of biotissues as the subject to be highlighted, highlighting tissue designation section 150 may be provided with a function to receive a designation input designating a plurality of H ($H \leq J$) of biotissues in an overlapping manner (J is the total number of conversion data for highlighting a specific tissue stored in conversion data storage section for highlighting a specific tissue 120). And when color conversion section for highlighting a specific tissue 160 receives a designation input designating a plurality of H biotissues from highlighting tissue designation section 150, color conversion using a plurality of H conversion data for highlighting specific tissue corresponding to the plurality of H biotissues is carried out in an overlapping manner to generate specific tissue highlighted graphic data.

Also, highlighting tissue designation section 150 may also receive a designation input that "no biotissue is designated" (hereinafter referred to as an "empty designation input"). When there is the "empty designation input", color conversion section for highlighting a specific tissue 160 outputs the input standard color graphic data Ds as it is, without carrying out any substantial color conversion process. In this case, standard color graphic data Ds will be output as it is, as specific tissue highlighted graphic data Ds. Certainly, the display on the color monitor using this specific tissue highlighted graphic data Ds will be a graphic wherein no biotissue is highlighted.

In short, in the example described here, highlighting tissue designation section 150 has a function of receiving an empty designation input indicating that no biotissue is designated, and color conversion section for highlighting a specific tissue 160 outputs standard color graphic data Ds as it is, as specific tissue highlighted graphic data without carrying out color conversion, when an empty designation input is received from highlighting tissue designation section 150.

Certainly, a dedicated color correction device 100 may be provided that highlights only a specific biotissue at all times. For example, in an example used in an environment wherein only the "blood vessel" needs to be highlighted and other biotissue is not need to be highlighted, only blood vessel highlighted data Ce needs to be stored in conversion data storage section for highlighting a specific tissue 120. In this case, when color conversion section for highlighting a specific tissue 160 carries out color conversion, color conversion using blood vessel highlighted data Ce is always carried out, and specific tissue highlighted graphic data De is always output. Certainly, highlighting tissue designation section 150 may be provided with a function of receiving an empty designation input, also in this case. In such a case, the designation input to highlighting tissue designation section 150 is an input that selects whether to highlight (input to designate the blood vessel) or not (empty designation input).

Also, when highlighting tissue designation section 150 is provided with a function of receiving different designation inputs for each color monitor 50A-50D, a graphic wherein different biotissue is highlighted may be displayed respectively for each color monitor 50A-50D. For example, with respect to highlighting tissue designation section 150, when an empty designation input is input to color monitor 50A, designation of "blood vessel" is input to color monitor 50B, designation of "fat" is input to color monitor 50C, and designation of "surface layer" is input to color monitor 50D, color conversion section for highlighting a specific tissue 160 may output four types of specific tissue highlighted graphic data Ds, De, Df, and Dg.

In this case, color conversion section for a monitor 170 may carry out color conversion using individual conversion data Ca to graphic data Ds to generate display data Da, carry out color conversion using individual conversion data Cb to graphic data De to generate display data db, carry out color conversion using individual conversion data Cc to graphic data Df to generate display data Dc, and carry out color conversion using individual conversion data Cd to graphic data Dg to generate display data Dd. Thereby, a standard color graphic is displayed on color monitor 50A, a graphic wherein "blood vessel" is highlighted is displayed on color monitor 50B, a graphic wherein "fat" is highlighted is displayed on color monitor 50C, and a graphic wherein "surface layer" is highlighted is displayed on color monitor 50D.

<2.3 Basic Operation Relating Third Conversion Process>

Finally, the basic functions of individual conversion data storage section for a monitor 130 and color conversion section for a monitor 170 relating to the third conversion process (a process carried out to specific tissue highlighted graphic data De, Df, and Dg, for example, output from color conversion section for highlighting a specific tissue 160) will be described.

First, individual conversion data storage section for a monitor 130 is a component configured to store individual conversion data Ca-Cd corresponding to each color monitor 50A-50D. These individual conversion data Ca-Cd are conversion data for carrying out color conversion such that a graphic having a standard color property is displayed on specific color monitors 50A-50D, in consideration of the peculiar color property of each corresponding specific color monitor 50A-50D.

Meanwhile, color conversion section for a monitor 170 is a component configured to generate display data by carrying out color conversion, to the specific tissue highlighted graphic data given from color conversion section for highlighting a specific tissue 160, using the individual conversion data for the specific color monitor stored in individual conversion data storage section for a monitor 130, and to output the generated display data to the specific color monitor. For example, in a case of an example wherein specific tissue highlighted graphic data De highlighting a "blood vessel" is given from color conversion section for highlighting a specific tissue 160 to color conversion section for a monitor 170, and graphic based on this graphic data De is displayed on the first color monitor 50A, display data Da is generated by carrying out color conversion, to specific tissue highlighted graphic data De, using individual conversion data Ca for the first color monitor 50A stored in individual conversion data storage section for a monitor 130, and generated display data Da is output to the first color monitor 50A.

As described above, each individual conversion data Cx-Cz stored in individual conversion data storage section for an imaging device 110 are data for carrying out conversion to eliminate the difference in peculiar color property of medical imaging devices 30X-30Z, and color conversion section for an imaging device 140 carries out a process of generating standard color graphic data Ds by eliminating the difference in such peculiar color property. Meanwhile, each individual conversion data Ca-Cd stored in individual conversion data storage section for a monitor 130 are data for carrying out conversion to eliminate the difference in peculiar color property of color monitors 50A-50D, and color conversion section for a monitor 170 carries out a process of generating display data Da-Dd suitable for each color monitor 50A-50D, so that the difference in such peculiar color property is eliminated, and a display having the identical tint may be carried out on the screens of all color monitors.

In the illustrated example, since four color monitors 50A-50D are connected to color correction device for a medical apparatus 100, four sets of individual conversion data Ca-Cd are prepared in individual conversion data storage section for a monitor 130. However, generally, when the use of a plurality of K color monitors is assumed, the individual conversion data for these K medical imaging devices may be stored respectively in individual conversion data storage section for a monitor 130. In this case, when generating display data Dk to be output to the k-th ($1 \leq k \leq K$) color monitor 50k, color conversion section for a monitor 170 may carry out color conversion using the k-th individual conversion data Ck (individual conversion data for the k-th color monitor 50k).

In this way, when the identical graphic data are given to a plurality of color monitors having color property different to each other and displayed thereon, the technique itself to carry out color conversion to graphic data using the individual conversion data prepared for each color monitor, in order to make the tint of the display graphics displayed on the screen of each color monitor identical, is already known in the art. In particular, in the case of a color monitor used by a professional such as a printing company, individual conversion data (generally referred to as color profile data) in consideration of a color property peculiar to the color monitor is often prepared in advance. Thus, when the color profile data is attached to the color monitor, the color profile data may be used as the individual conversion data to be stored in individual conversion data storage section for a monitor 130. As described above, since a method for generating the color profile data peculiar to each color monitor is also already known, a detailed description thereof is omitted here.

<2.4 Features of Color Correction Device for Medical Apparatus According to Present Invention>

As described above, in color correction device for a medical apparatus 100 according to the present invention, the three-stage color conversion process, such as the first conversion process by color conversion section for an imaging device 140, the second conversion process by color conversion section for highlighting a specific tissue 160, and the third conversion process by color conversion section for a monitor 170, is carried out.

The first conversion process and the third conversion process fulfill a role to eliminate the difference in color property among apparatuses, and these processes achieve the first object of the present invention "to eliminate differences in color property among apparatuses and to enable graphic display with a uniform color tone even when a medical graphic display system is constituted by combining apparatuses having various color property".

Also, the second conversion process fulfills a role to highlight a specific biotissue designated by an operator, and this process achieves the second object of the present invention "to enable a graphic display with visibility that is suitable for the examination of a specific biotissue, when utilizing a medical graphic display system". For example, as will be described in detail later, when an operator designates a specific biotissue such as a "blood vessel", "fat," or "surface layer" as a subject of highlighted display, a display with more improved visibility of the designated biotissue may be obtained. For example, in a conventional system, the color of blood that has been saturated at the imaging stage, may be accurately read on a color monitor.

In addition, since the second conversion process is carried out between the first conversion process and the third conversion process, the second conversion process may be carried out as a process to standard color graphic data Ds obtained by the first conversion process. Therefore, when the second conversion process is carried out, it is not necessary to consider the "color property peculiar to the apparatus" such as a color property of each medical imaging device, and it is sufficient to carry out a uniform color correction at all times, whose processing subject is standard color graphic data Ds having the standard color property. Also, since the third conversion process is carried out after the second conversion process, when the second conversion process is carried out, there is no need to consider the "color property peculiar to the apparatus" such as color property of the color monitor on which graphic is finally displayed. In other words, in conversion data storage section for highlighting a specific tissue 120, it is sufficient to prepare a uniform conversion data for highlighting specific tissue at all times, regardless of the type of medical imaging device or color monitor actually used.

In this manner, color correction device for a medical apparatus 100 according to the present invention may be used without considering the differences in color property between the models, regardless of the models and the providers of the medical imaging device connected to the input-side, and the models and the provider of the color monitor connected to the output-side. For this reason, color determination based on a similar criterion will be possible in any facility provided with medical graphic display system 1000 according to the present invention, in any of the hospitals and the research facilities.

<<< § 3. Substance of Individual Conversion Data for Imaging Device>>>

Here, the substance of individual conversion data for imaging device Cx, Cy, and Cz stored in individual conversion data storage section for an imaging device 110, that is a component of color correction device for a medical apparatus 100 illustrated in FIG. 3, will be described in more detail. As already described in § 2 above, the individual conversion data Cx, Cy, and Cz are conversion data to convert color property of each imaging data Dx, Dy, and Dz into the standard color property, in consideration of the peculiar color property of each corresponding medical imaging device 30X, 30Y, and 30Z. Here, the specific procedures to generate individual conversion data Cx for medical imaging device 30X will be described referring to the block diagram of FIG. 4.

Generally, graphic data handled by an imaging device and a color monitor device is composed of an aggregate of a large number of pixels. Each pixel usually has each pixel value of the three primary color components R, G, and B. For example, when one color component is represented by 8-bit data, the pixel value of one pixel is represented by 24-bit data. Therefore, when the pixel value of the individual pixels constituting imaging data Dx obtained from medical imaging device 30X are expressed with the three primary color components R-old, G-old, and B-old, and the pixel value of the individual pixels constituting standard color graphic data Ds obtained by color conversion by color conversion section for an imaging device 140 are expressed with the three primary color components R-new, G-new, and B-new, the individual conversion data Cx stored in individual conversion data storage section for an imaging device 110 will be conversion data to convert the three primary color components R-old, G-old, and B-old of imaging data Dx into three primary color components R-new, G-new, and B-new of standard color graphic data Ds. That is, some information that may uniquely determine another value (R-new, G-new, and B-new) based on an arbitrary value (R-old, G-old, and B-old) may be used as individual conversion data Cx.

Figure 4:
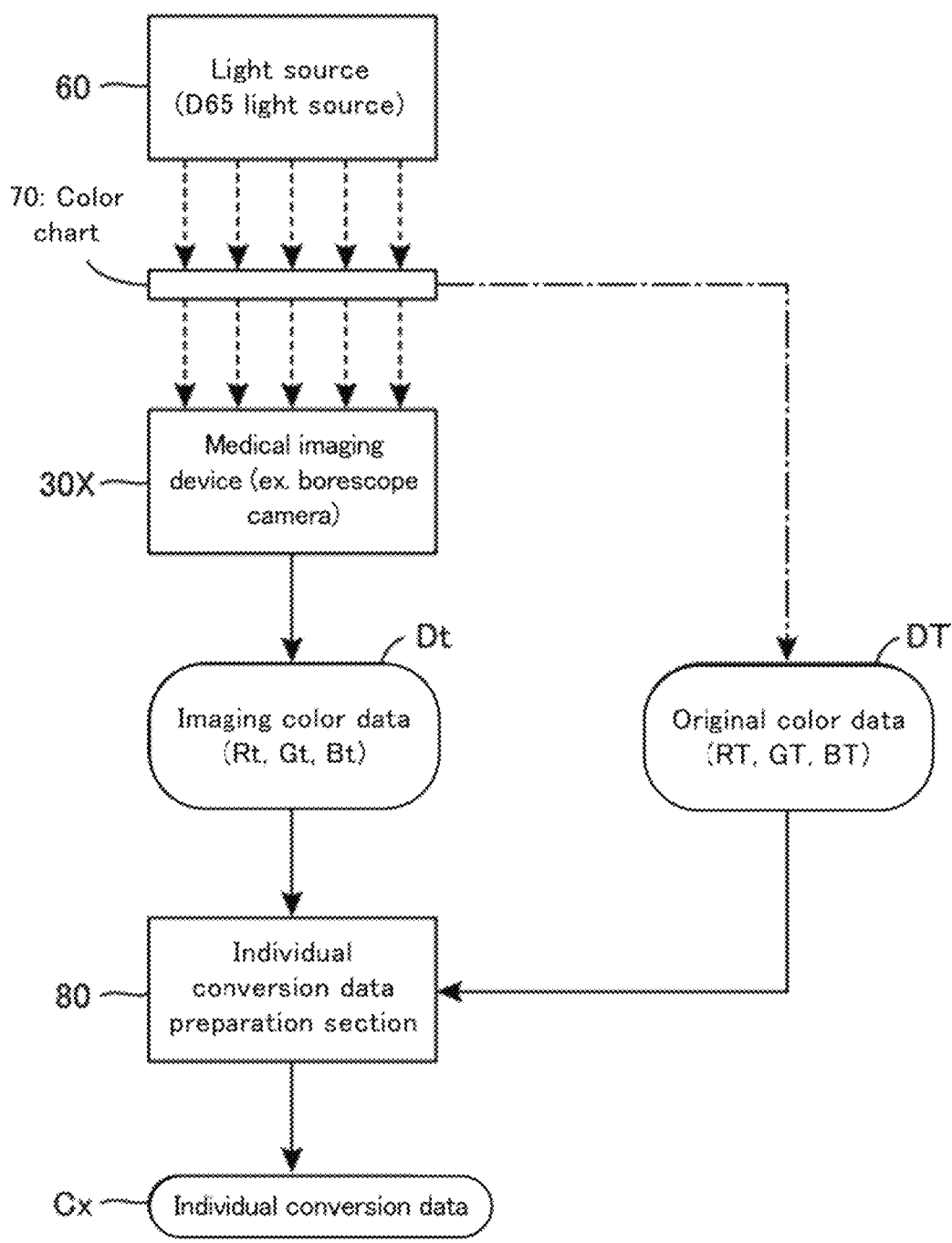
FIG. 4 is a block diagram illustrating a generating procedure of individual conversion data Cx to be stored in individual conversion data storage section for an imaging device 110 illustrated in FIG. 3.

In order to generate such individual conversion data Cx, actual measurement using a color chart presenting a color sample may be carried out. As illustrated in FIG. 4, white light source 60 and color chart 70 are prepared. In the example illustrated here, a light source according to the CIE standard light source D65 (hereinafter, simply referred to as "D65 light source") is used as white light source 60. This D65 light source is a standard light source defined by the Commission Internationale de l'eclairage (CIE), and is assumed to be a virtual light source with a spectrum equivalent to the average noon light in Europe/Northern Europe, with a correlated color temperature of approximately 6500K. Incidentally, the standard light source "D65 light source" itself is not an actually commercially available as a device. Therefore, in practical use, a commercially available device that emits light approximating the standard light source D65 (such as an LED light source) may be used as light source 60 illustrated in FIG. 4. The reason for using this D65 light source as a light source will be described in § 5.

Figure 5A:
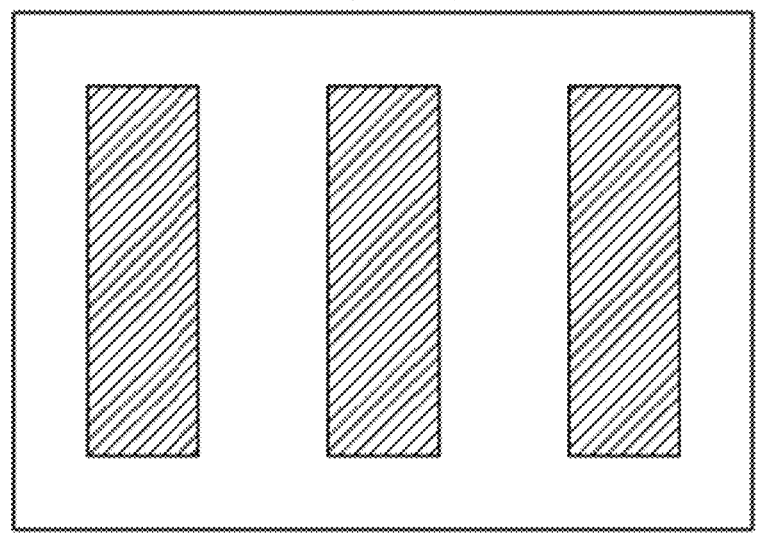
FIGS. 5A to 5C are plan views illustrating a specific example of color chart 70 illustrated in FIG. 4.
Figure 5B:
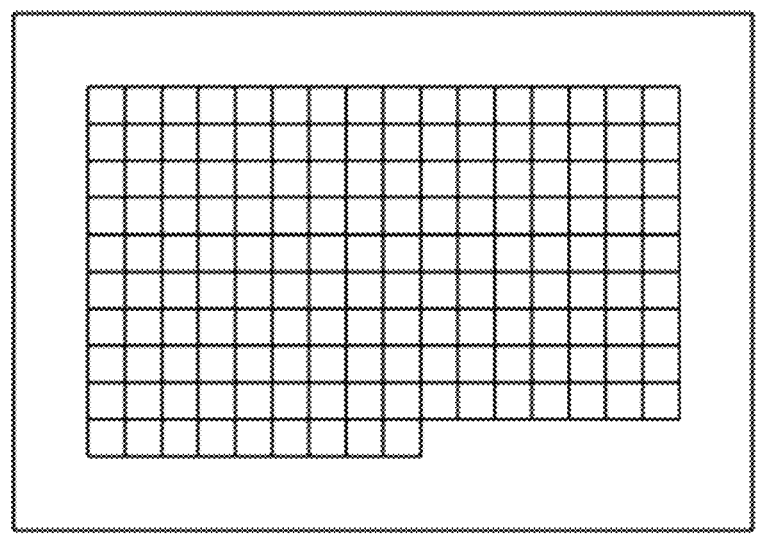
Figure 5C:
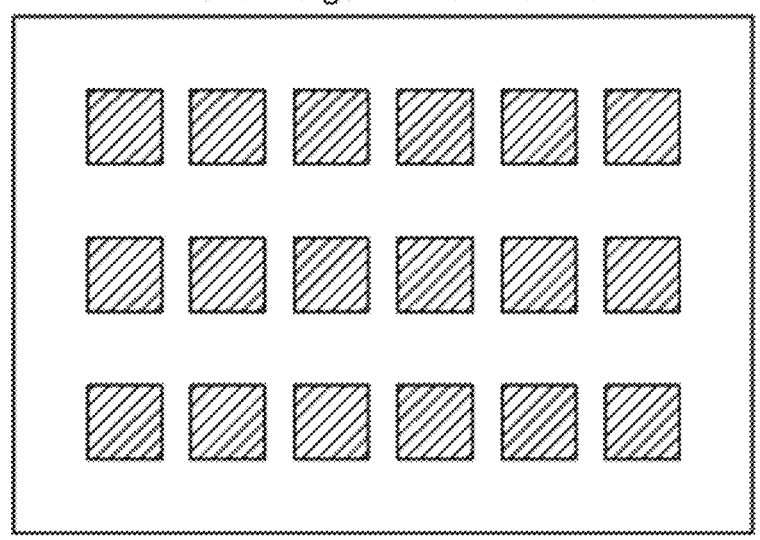

Meanwhile, color chart 70 is a plate-like object wherein color samples are arrayed, and is used to check color reproducibility and color calibration for various graphic apparatuses. A plan view of some specific examples of this color chart 70 is illustrated in FIGS. 5A, 5B, and 5C. Three primary color chart 71 illustrated in FIG. 5A is the simplest color chart wherein color samples of three primary colors of red, blue, and green are arranged. Three regions illustrated with hatching in the figures are portions of color samples of three primary colors, and have translucency to transmit red, blue, and green color components, respectively. Therefore, when white light source 60 is disposed on the back surface, and this three primary color chart 71 is observed from the front, the respective regions are observed as red, blue, and green windows.

Multicolor chart 72 illustrated in FIG. 5B arranges a large number of square-shaped color samples on a two-dimensional array, and is usually utilized to verify color reproducibility in low to medium saturation for cameras and monitors. While only color samples of the three primary colors of red, blue, and green are arranged in three primary color chart 71 illustrated in FIG. 5A, 153 color samples are arranged in multicolor chart 72 illustrated in FIG. 5B, enabling more detailed color calibration. Meanwhile, wide gamut color chart 73 illustrated in FIG. 5C is a color sample that covers a wide color gamut as specified by international specification BT.2020 for an ultra-high-definition TV, although the total number of color samples arranged is not so large. This wide gamut color chart 73 is suitable for verifying the color reproducibility of high-saturation colors and primary colors, and specific methods for calibrating colors using this are described in § 4.

Although three types of color charts 71, 72, and 73 are exemplified in FIGS. 5A-5C, various products are commercially available as the color charts, and the color charts used in the present invention are not limited to the three types illustrated in FIGS. 5A-5C. For example, in order to compensate for the medium saturation color, a color chart generally called a McBeth chart may be used.

Now, as illustrated in FIG. 4, light source 60 is arranged on the back side of color chart 70, medical imaging device 30X (such as endoscope camera) is arranged on the front side of color chart 70, and graphic on the front side of color chart 70 is imaged by medical imaging device 30X. The transmitted light within each color sample region of color chart 70 incident to the light receiving surface of medical imaging device 30X. The dashed arrows illustrated in FIG. 4 indicate the path of light from light source 60. Among imaging data thus obtained, the color components of the three primary colors (R, G, and B) in each color sample region of color chart 70 are referred to as imaging color data Dt (Rt, Gt, and Bt).

For example, when three primary color chart 71 illustrated in FIG. 5A is used as color chart 70, imaging color data Dt1 (Rt1, Gt1, and Bt1) for the red region, imaging color data Dt2 (Rt2, Gt2, and Bt2) for the green region, and imaging color data Dt3 (Rt3, Gt3, and Bt3) for the red region are obtained. Similarly, when multicolor chart 72 illustrated in FIG. 5B is used as color chart 70, imaging color data Dt 1 (Rt1, Gt1, and Bt1) for the first color sample to imaging color data Dt153 (Rt153, Gt153, and Bt153) for the 153rd color sample are obtained.

Meanwhile, original color data DT (RT, GT, and BT) is measured for each color sample of color chart 70. The dashed arrows in FIG. 4 indicate that color data DT is obtained using such a measurement process. For example, when three primary color chart 71 illustrated in FIG. 5A is used as color chart 70, original color data DT1 (RT1, GT1, and BT1) for the red region, original color data DT2 (RT2, GT2, and BT2) for the green region, and original color data DT3 (RT3, GT3, and BT3) for the blue region are obtained. Similarly, when multicolor chart 72 illustrated in FIG. 5B is used as color chart 70, original color data DT 1 (RT1, GT1, and BT1) for the first color sample to original color data DT153 (RT153, GT153, and BT153) for the 153rd color sample are obtained.

For example, original color data DT may be measured by placing a spectroscopic analyzer (colorimeter) at the position of medical imaging device 30X illustrated in FIG. 4 to measure the spectrum for each of the regions of the individual color sample (a measurement system similar to that illustrated in FIG. 7A to be described later may be used) and calculating the values of the three primary color components (RT, GT, and BT) based on the data of this spectrum. There are some cases, however, wherein original color data DT (RT, GT, and BT) obtained by measurement at the supplier is attached to the commercially available color chart 70. In such cases, the measurement operation may be omitted and the attached original color data DT (RT, GT, BT) may be used as it is.

When imaging color data Dt (Rt, Gt, and Bt) and original color data DT(RT, GT, and BT) are obtained for the identical color chart 70 in this manner, these data are given to individual conversion data preparation section 80 to obtain the individual conversion data Cx. Actually, individual conversion data preparation section 80 is a device constituted by incorporating a dedicated program to a computer, and recognizes a color property peculiar to medical imaging device 30X based on the difference between imaging color data Dt (Rt, Gt, and Bt) and original color data DT (RT, GT, and BT) for respective color samples, and generates individual conversion data Cx for matching imaging color data Dt (Rt, Gt, and Bt) with original color data DT (RT, GT, and BT).

When three primary color chart 71 illustrated in FIG. 5A is used, individual conversion data Cx (data enabling conversion for an arbitrary color) is needed to be generated based on comparison results of the data Dt (Rt, Gt, and Bt) and data DT (RT, GT, and BT) with respect to the three color samples, respectively, so that the accuracy of the obtained individual conversion data Cx becomes relatively coarse. Meanwhile, when multicolor chart 72 illustrated in FIG. 5B is used, individual conversion data Cx may be generated based on the comparison results of data Dt (Rt, Gt, and Bt) and data DT (RT, GT, and BT) for the 153 color samples, respectively, so that individual conversion data Cx with higher accuracy may be obtained. Since the process of generating the individual conversion data Cx based on the comparison results of data Dt (Rt, Gt, and Bt) and data DT (RT, GT, and BT) for some color samples is a process known as a process of color calibration a described above, the explanation of specific processing algorithms in individual conversion data preparation section 80 is omitted here.

As described above, individual conversion data Cx is conversion data for converting three primary color components R-old, G-old, and B-old of the individual pixels constituting imaging data Dx obtained from medical imaging device 30X into three primary color components R-new, G-new, and B-new of the individual pixels constituting standard color graphic data Ds. Such individual converted data Cx may be prepared in the form of lookup table LUT, for example, as illustrated in FIG. 6A. The left-hand half of the table in FIG. 6A indicates three primary color components R-old, G-old, and B-old of the individual pixels constituting graphic data (imaging data D x) before conversion, and the right-hand half indicates three primary color components R-new, G-new, and B-new of the individual pixels constituting graphic data (standard color graphic data Ds) after conversion. This example is an example wherein each color component is represented by a numerical value of 8 bits (0-255), and the left-hand half of the table is provided with 256×256×256 columns from (0, 0, 0) to (255, 255, 255), and the right-hand half of the table is provided with new color component values corresponding to these respective columns.

Therefore, when an arbitrary combination of pixel values indicating three primary color components (l, m, and n) is given, this may be converted into a predetermined combination of pixel values (l', m', and n'), by using the individual conversion data composed of this lookup table LUT. As described above, individual conversion data Cx stored in individual conversion data storage section for an imaging device 110 may be composed of lookup table LUT that converts the combination of each color component of pixels constituting imaging data Dx into the combination of each color component of pixels constituting standard color graphic data Ds.

Also, the individual conversion data Cx may also be prepared in the form of a mathematical function as illustrated in FIG. 6B. In this case, a mathematical function for calculating the combination of each color component of the pixels constituting standard color graphic data Ds may be prepared by providing the combination of each color component of the pixels constituting imaging data Dx as a variable value, and this mathematical function may be stored in individual conversion data storage section for an imaging device 110 as individual conversion data Cx.

For example, when the relation between three primary color components (R-old, G-old, and B-old) and (R-new, G-new, and B-new) in lookup table LUT illustrated in FIG. 6A may be expressed with mathematical functions f1, f2, and f3 such as:

$R\text{-new}=f1(R\text{-old}, G\text{-old}, \text{and } B\text{-old})$ $G\text{-new}=f2(R\text{-old}, G\text{-old}, \text{and } B\text{-old})$ $B\text{-new}=f3(R\text{-old}, G\text{-old}, \text{and } B\text{-old})$, the above functions f1, f2, and f3 may be used as individual conversion data Cx, instead of lookup table LUT. Generally speaking, it is difficult to find a mathematical function that may carry out exactly identical conversion as the conversion with lookup table LUT. However, when the mathematical function may be approximated to the conversion with lookup table LUT to some degree, it is practically fine to use it as individual conversion data Cx.

For lookup table LUT relating 8-bit pixel value, as described above, 256×256×256 conversion data is required. Therefore, when lookup table LUT is used as individually converted data Cx, individual conversion data storage section for an imaging device 110 needs to secure some large storage capacity. Meanwhile, when the mathematical function is used as individual conversion data Cx, the storage capacity required for individual conversion data storage section for an imaging device 110 is greatly reduced.

Although an aspect of the lookup table LUT illustrated in FIG. 6A and an aspect of the mathematical functions illustrated in FIG. 6B have been exemplified above as the substance of the individual conversion data stored in individual conversion data storage section for an imaging device 110, the same aspect may be adopted for the individual conversion data stored in individual conversion data storage section for a monitor 130. That is, as the individual conversion data (such as data Ca) stored in individual conversion data storage section for a monitor 130, by giving a lookup table that converts a combination of each color component of pixels constituting a specific tissue highlighted graphic data (such as data De) into a combination of each color component of pixels constituting a display data (such as data Da), or a combination of each color component of pixels constituting specific tissue highlighted graphic data (such as data De), a mathematical function for calculating a combination of each color component of pixels constituting display data (such as data Da) may be used.

<<< § 4. Expansion to 4K8K Graphic System>>>

Recently, 4K8K satellite broadcasting has begun, and 4K TV and 8K TV enabling high-definition graphic display have begun to become popular even in ordinary homes. However, the currently commercially available medical graphic display system does not employ a color management platform for such a 4K8K graphic, and it is difficult to display a high-definition biotissue graphic on a color monitor. Therefore, the inventors of the present application have carried out searches on how much color reproducibility is obtained on a color monitor, with respect to the conventional common medical graphic display system illustrated in FIG. 1 and FIG. 2. Hereinafter, the measurement results will be described.

Figure 7A:
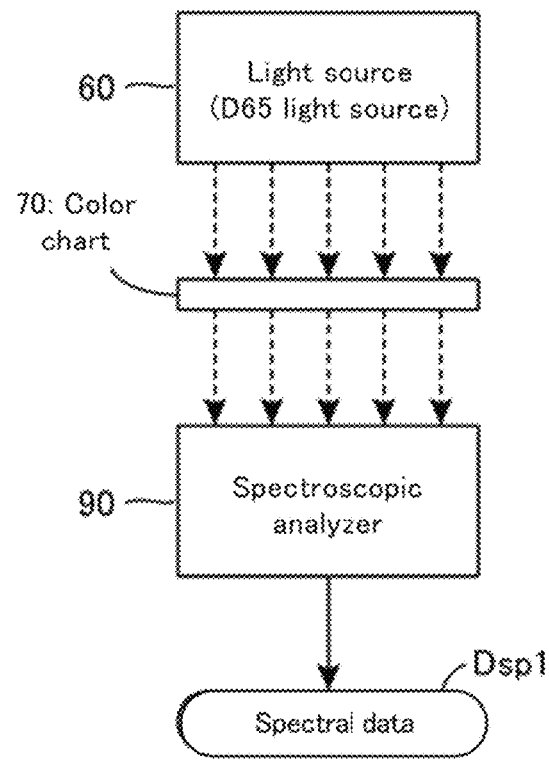
FIGS. 7A and 7B are diagrams illustrating a basic procedure of a measurement to examine color reproducibility on a color monitor, in relation to a medical graphic display system.
Figure 7B:
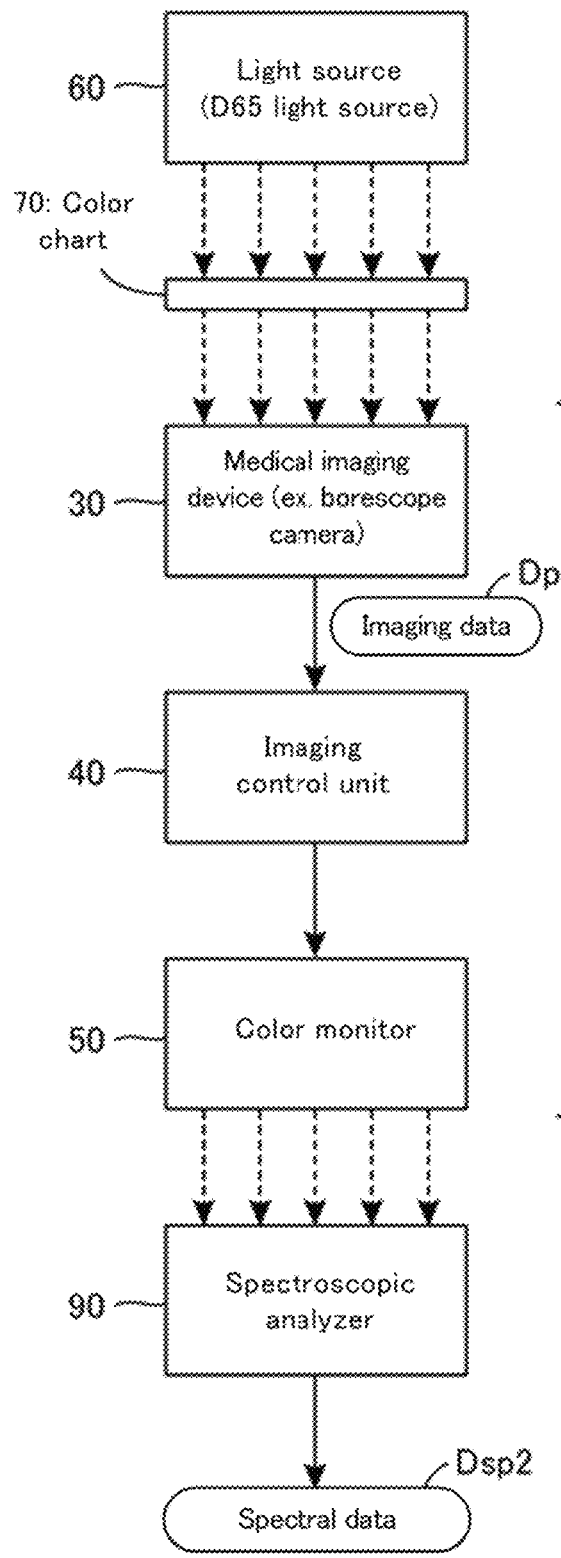

FIGS. 7A and 7B are diagrams illustrating a basic procedure of a measurement to examine color reproducibility on a color monitor, in relation to a medical graphic display system (the dashed lines in the figures indicate the light path). In the measurement described here, color chart 70 wherein a plurality of color samples are arranged, is used. In the first procedure illustrated in FIG. 7A, the original color of each color sample of this color chart 70 is measured. Meanwhile, in the second procedure illustrated in FIG. 7B, each color sample of this color chart 70 is imaged with the medical graphic display system, displayed on the color monitor, and the colors displayed on this color monitor are measured. Specifically, the measurement is carried out by the following method.

First, in the first procedure, as illustrated in FIG. 7A, light source 60 is disposed on the back surface of color chart 70, spectroscopic analyzer 90 is disposed on the front surface of color chart 70, and the spectrum of the transmitted light from each color sample disposed on color chart 70 is measured to obtain spectral data Dsp1. For example, when multicolor chart 72 illustrated in FIG. 5B is used as color chart 70, spectral data Dsp1 of the transmitted light is obtained respectively for all 153 sets of color samples.

Meanwhile, in the second procedure, as illustrated in FIG. 7B, light source 60 is disposed on the back surface of color chart 70, medical imaging device 30 (such as endoscope camera) is disposed on the front surface of color chart 70, and color chart 70 is imaged to obtain imaging data Dp. This imaging data Dp is given to color monitor 50 via imaging control unit 40, and the imaged color chart 70 is displayed on the screen of color monitor 50. Here, as illustrated in FIG. 2, medical imaging device 30, imaging control unit 40, and color monitor 50 are components of the medical graphic display system. Further, spectroscopic analyzer 90 is disposed on the front surface of color monitor 50, and spectrum of each color sample of color charts 70 displayed on color monitor 50 is measured to obtain spectral data Dsp2. For example, when multicolor chart 72 illustrated in FIG. 5B is used as the color chart 70, spectral data Dsp2 of transmitted light are obtained respectively for all 153 color samples.

The identical D65 light source is used as light source 60 used in FIGS. 7A and 7B, and the identical multicolor chart 72 is used as color chart 70. Therefore, the first procedure illustrated in FIG. 7A and the second procedure illustrated in FIG. 7B are common in that the identical subject (multicolor chart 72) is illuminated under the identical illumination environment (D65 light source). However, spectral data Dsp1 obtained in the former is a spectrum obtained by directly measuring the transmitted light of the color sample, whereas spectral data Dsp2 obtained in the latter is a spectrum obtained when the color sample is observed via medical graphic display system (medical imaging device 30, imaging control unit 40, and color monitor 50). Incidentally, although endoscope camera is used as medical imaging device 30, the measurement is carried out with the endoscope light source built in this endoscope camera in the off-state. That is, in the second procedure illustrated in FIG. 7B, the light source for illuminating color chart 70 is only light source 60 (D65 light source).

Figure 8A:
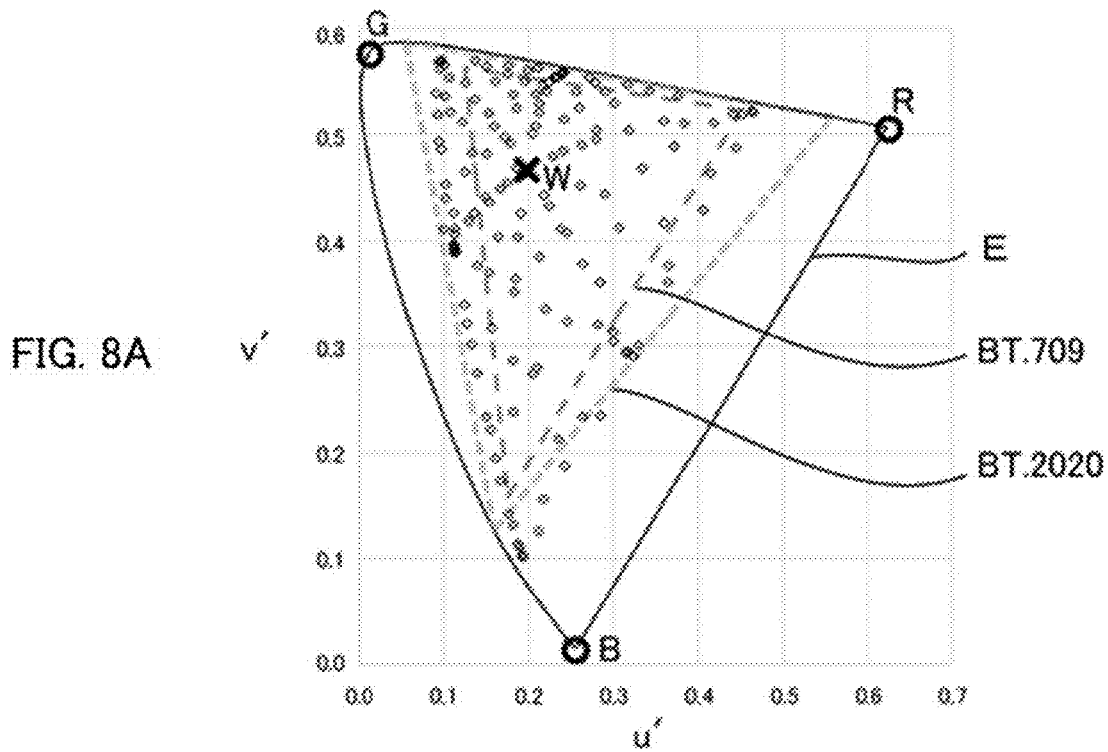
FIGS. 8A and 8B are u'v' chromaticity diagrams illustrating the color distribution obtained by the measurement procedure illustrated in FIGS. 7A and 7B, to multicolor chart 72 illustrated in FIG. 5B.
Figure 8B:
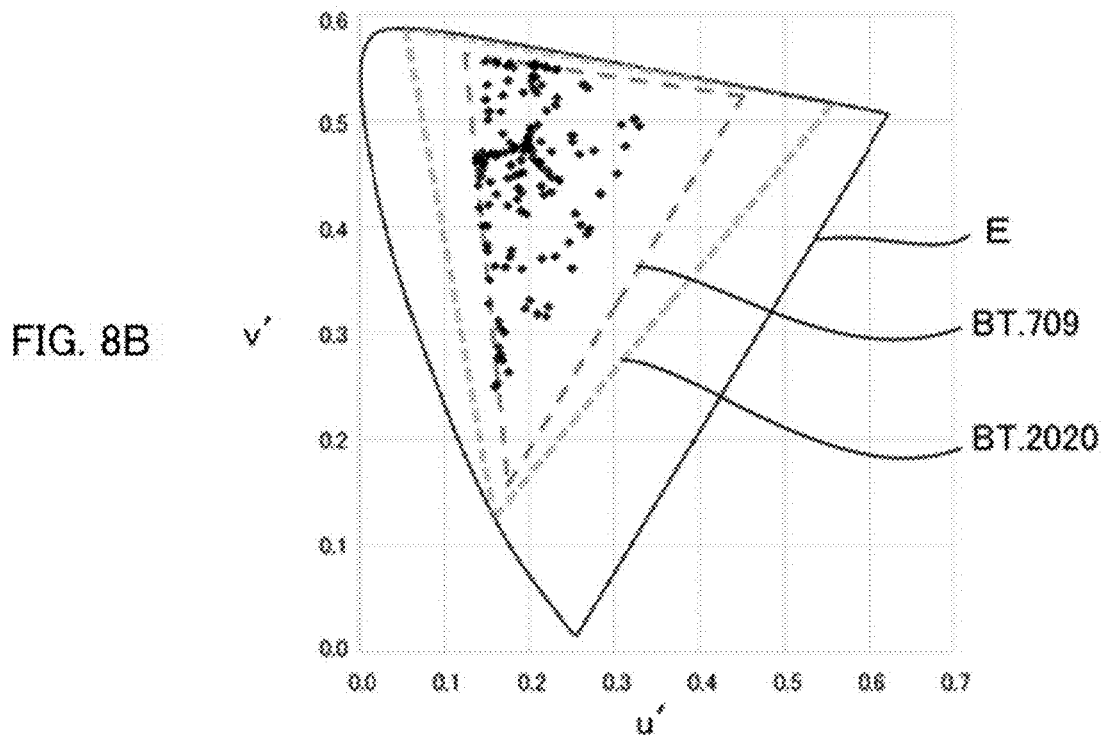

Therefore, by comparing spectral data Dsp1 with spectral data Dsp2, the color reproducibility when observed through the medical graphic display system may be evaluated. Generally, a two-dimensional chromaticity diagram is used when evaluating the color reproducibility. Here, as a two-dimensional chromaticity diagram, the results of the color reproducibility evaluated using u'v' chromaticity diagram are shown. FIGS. 8A and 8B illustrates examples of such evaluation results, and are u'v' chromaticity diagrams illustrating the color distribution obtained by the measurement procedure illustrated in FIGS. 7A and 7B, to multicolor chart 72 illustrated in FIG. 5B.

Specifically, in FIG. 8A, the colors corresponding to spectral data Dsp1, obtained by the first procedure illustrated in FIG. 7A, are plotted in u'v' chromaticity diagram. This illustrates the original color distribution of multicolor chart 72 itself (measured value under D65 light source) illustrated in FIG. 5B. As described above, total of 135 sets of color samples are arranged in multicolor chart 72, and in the first procedure illustrated in FIG. 7A, spectral data Dsp1 is obtained respectively for the 135 sets of color samples. Therefore, u'v' value for each color sample is calculated based on the respective spectral data Dsp1, and the values are plotted in u'v' chromaticity diagram, whereby the color distribution illustrated in FIG. 8A is obtained. The small white squares plotted indicate the colors of each color sample. Incidentally, since a method for calculating a predetermined color value (such as RGB value, tristimulus value, and u'v' value) based on an arbitrary spectral data is a known method known from a long time ago, a specific description thereof will be omitted here.

Similarly, in FIG. 8B, the colors corresponding to spectral data Dsp2, obtained by the second procedure illustrated in FIG. 7B, are plotted in u'v' chromaticity diagram. This illustrates the color distribution (imaged under D65 light source) obtained by observing multicolor chart 72 illustrated in FIG. 5B through a conventional medical graphic display system (observing the screen on color monitor 50). Also in the second procedure illustrated in FIG. 7B, spectral data Dsp2 is obtained respectively for the 135 color samples. Therefore, u'v' value for each color sample is calculated based on the respective spectral data Dsp2, and the values are plotted in u'v' chromaticity diagram, whereby the color distribution illustrated in FIG. 8B is obtained. The small black squares plotted indicate the colors of each color samples.

Next, u'v' chromaticity diagram illustrated in FIG. 8A will be observed in detail. In this diagram, abscissa axis is u' axis, ordinate axis is v' axis, and an arbitrary coordinate point (u', v') corresponds to a specific color. Thus, the tiny white squares plotted respectively indicate the color of a specific color sample. Point R, point G, and point B (indicated by open circles) plotted in this u'v' chromaticity diagram correspond to idealized red color, green color, and blue color, respectively, and regions close to triangles surrounded by solid lines passing through these points R, G, and B indicate real color region E wherein the colors actually present are distributed. While it is desirable for a graphic system to cover all of this real color region E, it is very difficult to realize such a graphic system. The borderline of this real color region E indicates the highest color saturation, and when it is traced to the point R-G-B along this borderline, the hue changes from the wavelength of 660 nm to 440 nm while maintaining high saturation. Point with reference numeral W in FIG. 8A (dots marked with x) is a point corresponding to white color.

As described above, in the two-dimensional u'v' chromaticity diagram, the distribution of the hue and the saturation may be illustrated. To indicate brightness, a brightness axis perpendicular to the plane of this u'v' chromaticity diagram (paper plane of the drawing) must be added to define a three-dimensional color space. For convenience of explanation, the color distribution of the hue and the saturation will be explained using the two-dimensional u'v' chromaticity diagram.

As used herein, u'v' chromaticity diagram depicts dashed triangles labeled "BT.709" and "BT.2020". Here, the triangle BT.709 indicates the color region specified in the specification of international specification BT.709 for a high-definition graphic TV, and a color monitor corresponding to a high-definition TV (equivalent to 2K) may display an arbitrary color within this color region. Meanwhile, triangles BT.2020 indicate color regions defined in the specifications of international specification BT.2020 for ultra-high-definition televisions, and color monitors compatible to 4K8K television may display an arbitrary color within these color regions. As illustrated in the figures, the region of triangle BT.2020 is wider than the region of triangle BT.709, and it may be understood that the color monitor compatible to 4K8K TV is capable of displaying a wider color gamut.

As described above, since FIG. 8A illustrates the original color distribution of multicolor chart 72 itself illustrated in FIG. 5B, the color distribution of the 135 sets of color samples themselves arranged in this multicolor chart 72 sufficiently covers the region of the triangle BT.709, and further covers the region of the triangle BT.2020 to some extent. However, when this multicolor chart 72 is observed through a conventional medical graphic display system, it may be understood that the color distribution thereof is considerably narrowed as illustrated in FIG. 8B. In other words, on color monitor 50 of the conventional medical graphic display system, the original color distribution of the subject (biotissue) is not sufficiently reproduced, and the color reproducibility is considerably lowered as compared with a case wherein the subject is directly viewed with the naked eye. In particular, in the case of this conventional system, the orange color is divided into yellow and red on the color monitor, and the intermediate color is reduced to highlight yellow and red.

The inventors of the present application have carried out the measurement of the basic procedure illustrated in FIGS. 7A and 7B with respect to another color chart. That is, the results illustrated in FIGS. 8A and 8B are for an example using multicolor chart 72 illustrated in FIG. 5B as a subject; instead, similar measurement using wide gamut color chart 73 illustrated in FIG. 5C as a subject was carried out. Here, wide gamut color chart 73 was originally developed by the applicant of the present application, for color management for 4K8K graphic, and is a color chart wherein color samples required to cover the region of the triangle BT.2020 are arranged. As described above, since the structure of the color charts, having a wide color gamut compatible to the color management for 4K8K graphic, is described in detail in International Publication WO2017/170910 and in the specification of International Application PCT/JP2018/038780, detailed descriptions thereof are omitted here.

As described above, FIGS. 9A and 9B are u'v' chromaticity diagrams illustrating the color distribution obtained by the measurement procedure illustrated in FIGS. 7A and 7B, to wide gamut color chart 73 illustrated in FIG. 5C. Specifically, in FIG. 9A, the color corresponding to spectral data Dsp1, obtained by the first procedure illustrated in FIG. 7A, are plotted in u'v' chromaticity diagram, and illustrates the original color distribution (measured values under D65 light source) of wide gamut color chart 73 itself. A total of 18 sets of color samples are arranged in wide gamut color chart 73, and the white squares plotted indicate the colors of these color samples. Meanwhile, in FIG. 9B, the color corresponding to spectral data Dsp2, obtained by the second procedure illustrated in FIG. 7B, are plotted in u'v' chromaticity diagram, and illustrates the color distribution (imaged under D65 light source) obtained by observing wide gamut color chart 73 through the conventional medical graphic display system (observing the screen of color monitor 50). The black squares plotted indicate the colors of the individual color samples.

Point RR, point GG, and point BB (indicated by white squares) illustrated in FIG. 9A indicate the colors of the red color sample, the green color sample, and the blue color sample, respectively, arranged in wide gamut color chart 73. As described above, the color distributions of the 18 sets of color samples themselves arranged in wide gamut color chart 73 sufficiently cover the region of the triangles BT.2020. However, when this wide gamut color chart 73 is observed through a conventional medical graphic display system, it is understood that the color distribution is considerably narrowed as illustrated in FIG. 9B, and does not sufficiently cover even the region of the triangle BT.709. Specifically, in the case of this conventional system, on the color monitor, the saturation of the red-based color is greatly reduced, the hue change of the yellow-based color to the green direction occurs, the saturation of the blue-based color is reduced, as well as the hue change to the cyan direction occurs.

Figure 10:
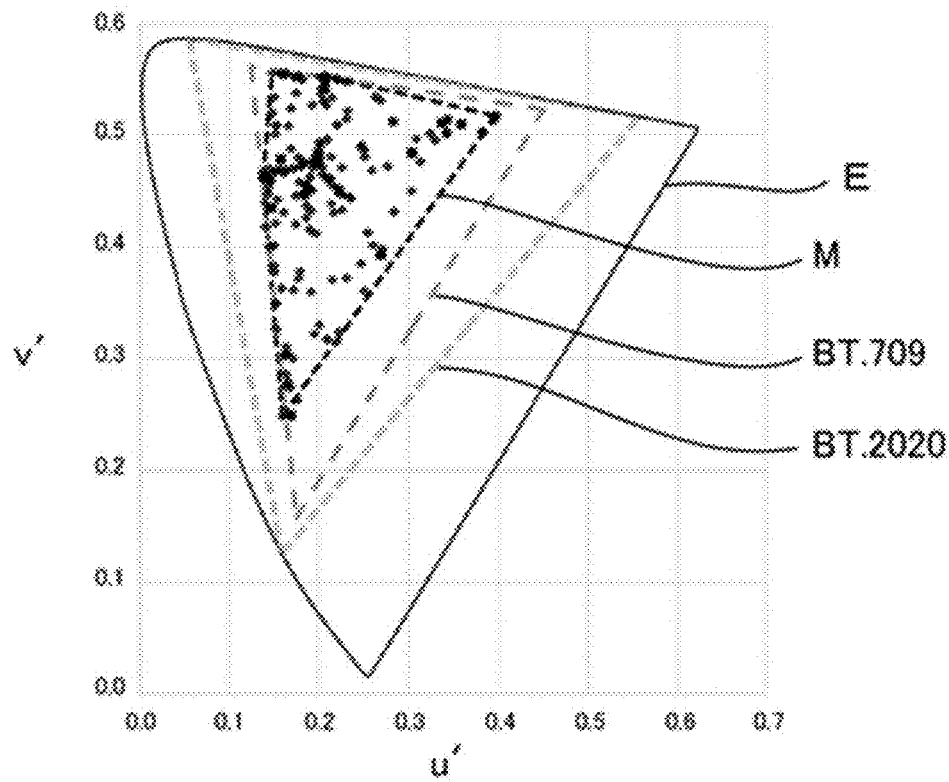
FIG. 10 is a u'v' chromaticity diagram illustrating a synthesized color distribution synthesizing the color distribution illustrated in FIG. 8B and the color distribution illustrated in FIG. 9B (upper diagram), and a diagram illustrating the color gamut usage ratio for the color distribution (lower diagram).

The upper diagram of FIG. 10 is a u'v' chromaticity diagram illustrated a synthesized color distribution synthesizing the color distribution illustrated in FIG. 8B and the color distribution illustrated in FIG. 9B, so to speak, the diagram is a color distribution diagram when a color chart including both the color sample in multicolor chart 72 illustrated in FIG. 5B and the color sample in wide gamut color chart 73 illustrated in FIG. 5C is observed through a conventional medical graphic display system. In this color distribution diagram, the dots plotted in black indicate the colors of each color sample. A polygon M indicated by a broken line in the figure is a circumscribed polygon of these points, and indicates a color distribution region on the monitor screen.

Therefore, when calculating the ratio between the area of this color distribution region M (Area (M)) and the area of the triangle BT.709 (Area (BT.709)), the result of Area (M)/Area (BT.709)=63% was obtained, as illustrated in the lower part of FIG. 10. This indicates that the display screen on the color monitor of the conventional medical graphic display system uses only 63% of the color gamut of the high-definition monitor. Similarly, when calculating the ratio between the area of this color distribution region M (Area (M)) and the area of the triangle BT.2020 (Area (BT.2020)), the result of Area (M)/Area (BT.2020)=37% was obtained, as illustrated in the lower part of FIG. 10. This indicates that the display screen on the color monitor of the conventional medical graphic display system uses only 37% of the color gamut of the 4K8K monitor.

These results indicate that color gamut utilization in conventional medical graphic display system is considerably low. Therefore, in the future, it is preferable to introduce an apparatus that handles 4K8K graphic, also for the medical graphic display system, and to display a high-definition biotissue graphic captured by a high-definition camera, on a color monitor compatible to 4K8K.

From this viewpoint, in constructing medical graphic display system 1000 according to the present invention illustrated in FIG. 3, it is preferable to use an apparatus compatible to 4K8K graphic imaging as each medical imaging device 30X, 30Y, and 30Z, and to use an apparatus compatible to 4K8K graphic display as color monitors 50A-50D. Also, as color correction device for a medical apparatus 100 according to the present invention, it is preferable to carry out color management compatible to a wide color gamut of 4K8K graphic, on the assumption that an apparatus compatible to 4K8K graphic is connected and used. Thereby, the practitioner may carry out more detailed color determination than the conventional medical graphic display system.

Specifically, as the individual conversion data to be stored in individual conversion data storage section for an imaging device 110, conversion data capable of color conversion (color conversion wherein standard color graphic data Ds covering the wide color gamut, may be obtained) covering the wide color gamut specified in the specifications of international specification BT.2020 related to an ultra-high-definition TV may be used. In order to generate such conversion data, wide gamut color chart 73 illustrated in FIG. 5C may be used as color chart 70 in the block diagram illustrated in FIG. 4. Similarly, as the individual conversion data to be stored in individual conversion data storage section for a monitor 130, conversion data capable of color conversion (color conversion capable of displaying the color that covers the wide color gamut, on the color monitor) covering the wide color gamut specified in the specifications of international specification BT.2020 related to an ultra-high-definition TV may be used.

<<< § 5. Benefits of Using D65 Light Source>>>

In the foregoing § 3, the specific procedure to generate individual conversion data Cx for medical imaging device 30X have been described, referring to a block diagram in FIG. 4. In this procedure, "D65 light source" is used as light source 60. Therefore, the reason why it is preferable to use "D65 light source" as light source 60 when generating the individual converted data stored in individual conversion data storage section for an imaging device 110 will be described here.

Figure 11:
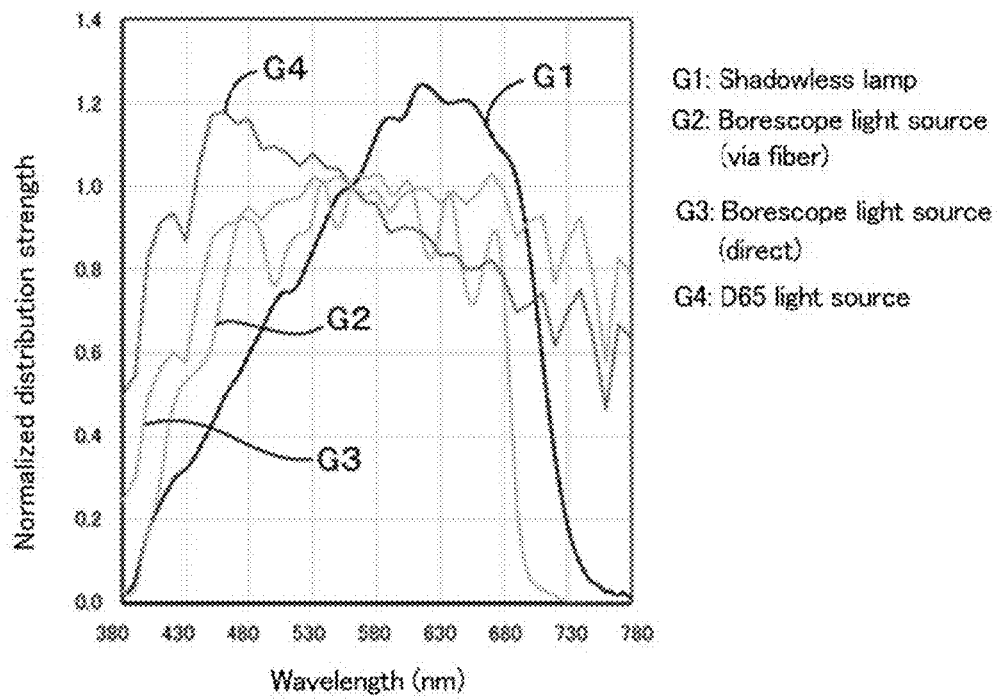
FIG. 11 is a graph illustrating the visible light spectrum of each light source.
Figure 12:
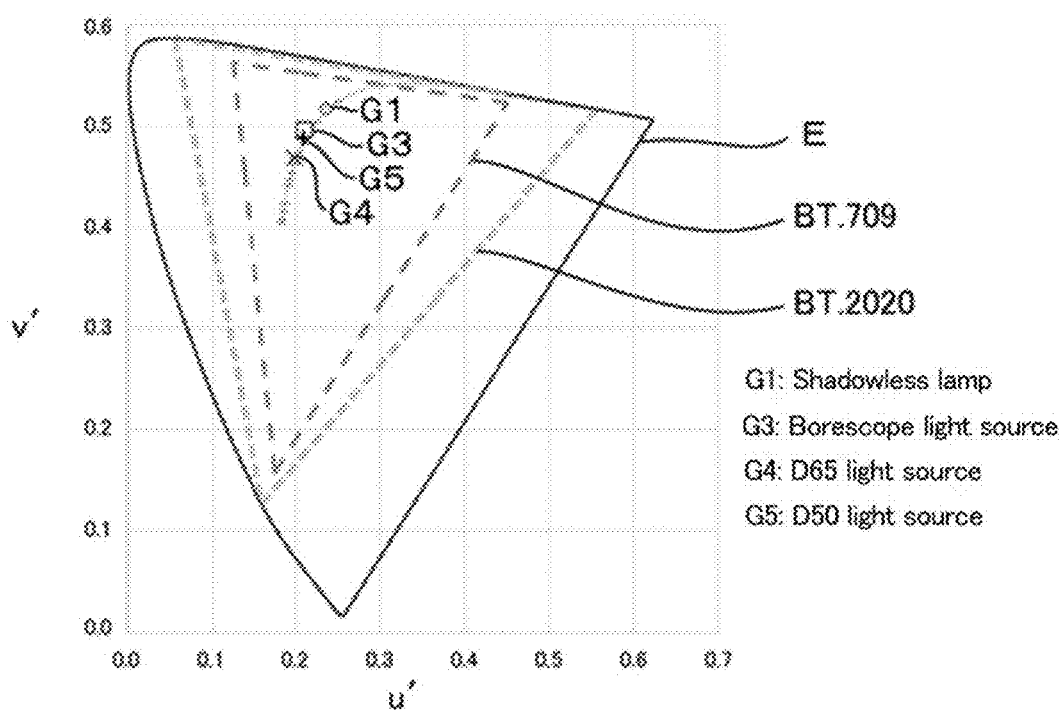
FIG. 12 is a u'v' chromaticity diagram illustrating the color temperature of each light source.

First, the spectrum of various light sources will be compared. FIG. 11 is a graph illustrating the visible light spectrum of each light source (ordinate axis is normalized so that the spectral intensity at 560 nm is 1.0). Here, graph G1 is spectrum of a shadowless lamp, graph G2 is spectrum of an endoscope light source (wherein light passed through a fiber is observed), graph G3 is spectrum of an endoscope light source (wherein light of a light source is directly observed), and the graph G4 is spectrum of spectrum of a D65 light source. Meanwhile, FIG. 12 is a u'v' chromaticity diagram illustrating the color temperature of each light source. Here, point G1 indicates the color temperature of shadowless lamp, point G3 indicates the color temperature of endoscope light source (direct observation of the light of the light source), point G4 indicates the color temperature of D65 light source, and point G5 indicates the color temperature of D50 light source. As described above, triangle BT.709 and triangle BT.2020 are color regions specified by the specifications of international specification BT.709 and BT.2020, respectively (the same applies to the following u'v' chromaticity diagram).

Referring to FIGS. 11 and 12, it may be understood that each of these light sources has considerable differences to each other in spectral waveform and also in color temperature. The results illustrated here are the results of measurements made using a specific shadowless lamp and a specific endoscope light source. In practice, however, the spectrum and color temperature of shadowless lamp and endoscope light source differ from product to product. Generally, halogen lamps are used for a shadowless lamp, and reddish illumination light with a color temperature of approximately 3400K is obtained. Also, a xenon lamp is usually used for endoscope light source, and white illumination light having a color temperature of approximately 4700K is obtained. Meanwhile, the light of D65 light source is a bluish illumination light having a color temperature of 6504K. Incidentally, D65 light source and D50 light source are standard light sources defined by the Commission Internationale de l'eclairage (CIE), and their spectra and color temperatures are defined by clear standards.

Generally, the light source used to illuminate the subject is a critical factor that influences tint when the subject is observed. Even for the identical subject, when the light source is different, the tint of the subject to be observed will be different. Therefore, in medical graphic display system illustrated in FIG. 3, the tint of obtained imaging data Dx-Dz differs according to the light source illuminating the subject (biotissue) to be imaged with medical imaging devices 30X-30Z.

Figure 13:
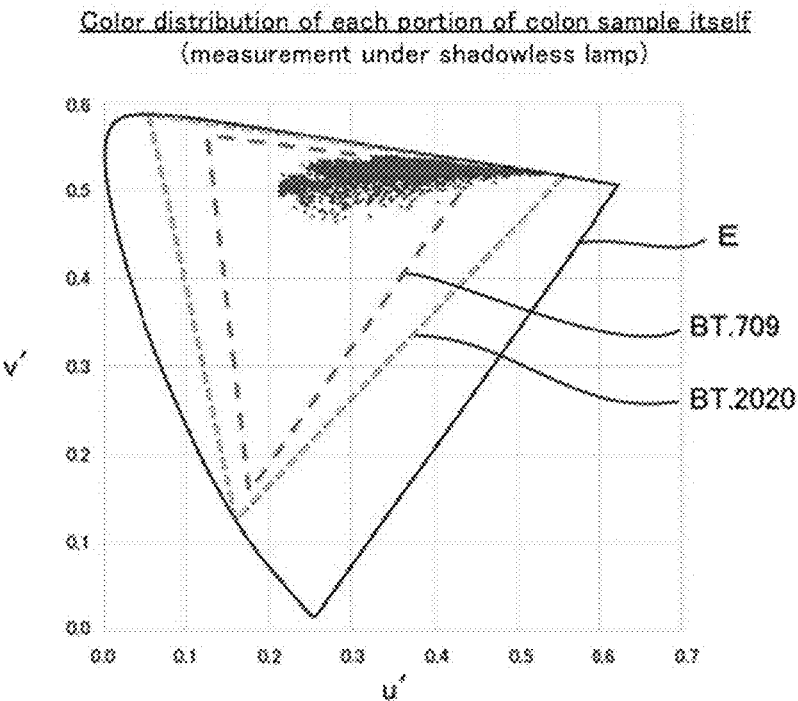
FIG. 13 is a u'v' chromaticity diagram illustrating the color distribution of each portion of the colon sample itself measured under a shadowless lamp.
Figure 14:
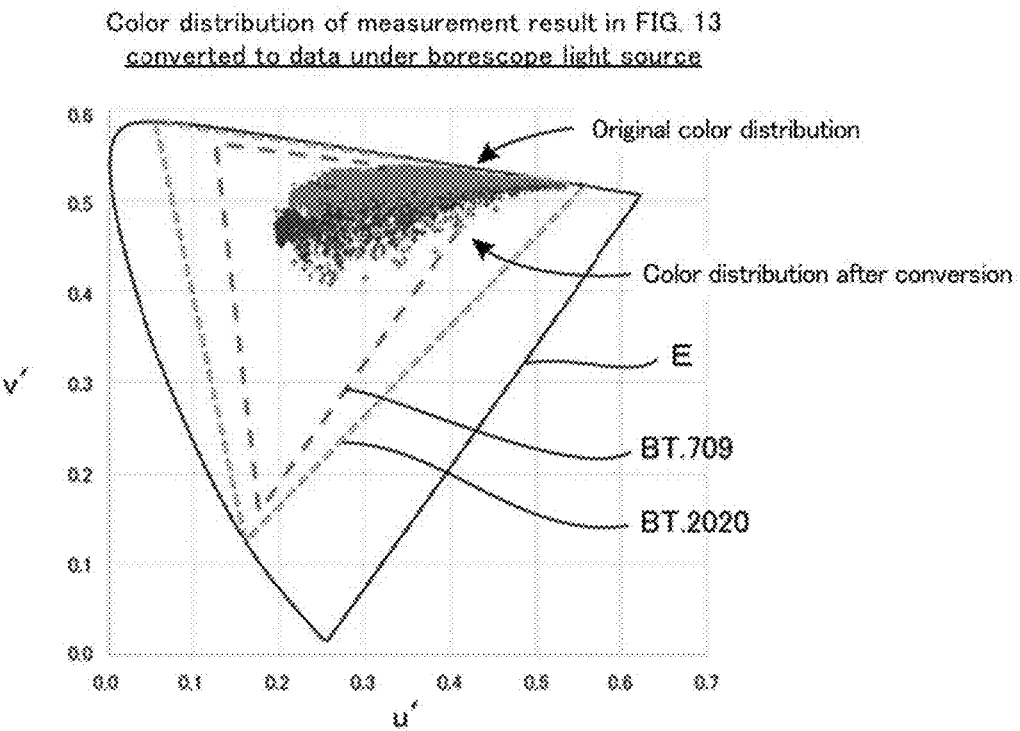
FIG. 14 is a u'v' chromaticity diagram illustrating the color distribution of each portion of the colon sample itself measured under an endoscope light source (via fiber) (actually converted data of the measurement result in FIG. 13 converted to the measurement result under endoscope light source by simulating).
Figure 15:
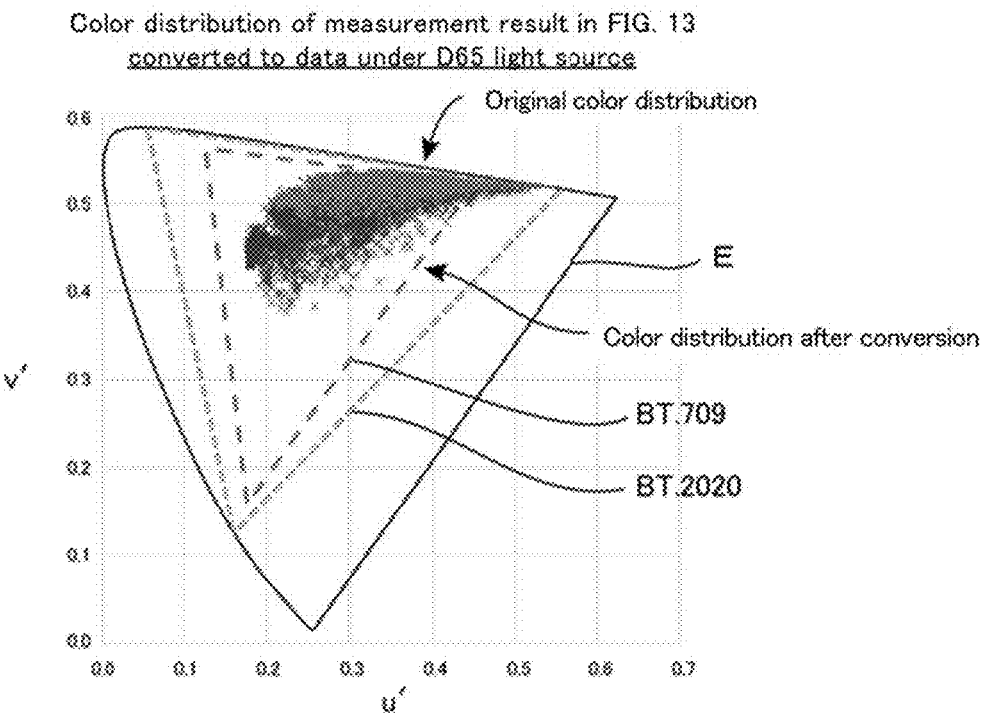
FIG. 15 is a u'v' chromaticity diagram illustrating the color distribution of each portion of the colon sample itself measured under D65 light source (actually converted data of the measurement result in FIG. 13 converted to the measurement result under D65 light source by simulating).

Therefore, the inventors of the present application have prepared an identical colon sample as a subject, and carried out experiments to compare the tint when this colon sample was illuminated with various light sources. FIGS. 13-15 are u'v' chromaticity diagram illustrating the results. First, FIG. 13 is a u'v' chromaticity diagram illustrating the color distribution of the respective portions of the colon sample itself under illumination by shadowless lamp, and illustrates the actual measurement results obtained by directly measuring the colors of a plurality of sample locations using spectroscopic analyzer, when the colon sample is illuminated by a shadowless lamp. The plot group including of a large number of black dots in the color distribution diagram of FIG. 13 indicates the color of each sample location. Each of them illustrates a color having a high saturation from red to orange.

Meanwhile, FIG. 14 is a u'v' chromaticity diagram illustrating the color distribution of each portion of the colon sample itself, under illumination by an endoscope light source (via fiber), and illustrates the results of measuring the color of a large number of sample locations, under a condition wherein the colon sample is illuminated with an endoscope light source via fiber. However, indeed, instead of actually measuring under the endoscope light source, the result of FIG. 14 is obtained by carrying out a simulation to convert the measurement result of FIG. 13 into the measurement result under endoscope light source, based on the spectrum difference illustrated in FIG. 11. In FIG. 14, the color distribution illustrated in FIG. 13 is also illustrated for convenience of comparison. That is, a plot group including a large number of black dots labeled "original color distribution" in the figure illustrates the measurement result under shadowless lamp illustrated in FIG. 13, and a plot group including a large number of + marks labeled "color distribution after conversion" in the figure illustrates the measurement result under endoscope light source (result after conversion by simulation). As illustrated in the figure, it may be understood that the "color distribution after conversion" is wider than the "original color distribution".

FIG. 15 is a u'v' chromaticity diagram illustrating the color distribution of each portion of the colon sample itself measured under illumination by D65 light source, and illustrates the results of measuring the colors of a large number of sample locations of the colon sample under illumination by D65 light source. However, also in this case indeed, instead of actual measurements under D65 light source, the results of FIG. 15 are obtained by carrying out a simulation wherein the measurement results of FIG. 13 are converted to those under D65 light source, based on the spectrum difference illustrated in FIG. 11. The color distribution illustrated in FIG. 13 is also illustrated in FIG. 15 for convenience of comparison. That is, the plot group including a large number of black dots labeled "original color distribution" in the figure illustrates the measurement result under shadowless lamp illustrated in FIG. 13, and the plot group including a large number of x marks labeled "color distribution after conversion" in the figure illustrates the measurement result under D65 light source (result after conversion by simulation). As illustrated in the figure, it may be understood that the "color distribution after conversion" is wider than the "original color distribution".

The results illustrated in FIGS. 13-15 show that the color distribution measured differs greatly according to the light source used, even though the completely identical colon sample is used as the subject. Focusing here on the broadness of the color distribution range, the relation of "under illumination by shadowless lamp"<"under illumination by endoscope light source"<"under illumination by D65 light source" is obtained. In particular, looking at the results illustrated in FIG. 15, it may be understood that the plot group of black dots (measurement results under illumination by shadowless lamp) labeled as "original color distribution" in the figure is distributed near the upper side of the triangle BT.2020, whereas the plot group of x (measurement results under illumination by D65 light source) labeled as "color distribution after conversion" in the figure is widely distributed in the region of the upper half of the triangle BT.2020. The examples illustrated here are the results of measurements with a specific colon sample as the subject. However, such a tendency is seen not only in the colon sample but also in various biotissue.

In general, when a photographed image of some subject is displayed on a color monitor, the wider the distribution range of colors, the expression using a larger number of colors is possible, so that visibility (the easiness to recognize one portion by visually separating it from another portion) may be improved. For example, in the example illustrated in FIG. 15, under illumination by shadowless lamp, expression using only a relatively highly saturated color (the color near the upper side of triangle BT. 2020) within the range labeled "original color distribution" is possible, while under illumination by D65 light source, expression using a lower saturation color within the wider range labeled "color distribution after conversion" (the color at the upper half of triangle BT.2020) is possible. Therefore, in order to improve visibility at least with respect to biotissue, it is preferable to carry out illumination by D65 light source rather than illumination by shadowless lamp or illumination by endoscope light source.

However, the results illustrated in FIGS. 13-15 do not necessarily indicate that illumination with D65 light source is superior to illumination with a shadowless lamp or endoscope light source, as the illumination used in surgery, but merely indicate that illumination with D65 light source is preferable from the viewpoint of improving visibility (in surgery, easiness of recognizing one tissue separately from another tissue). In fact, shadowless lamp has been used empirically as the light source for illuminating surgical table, and endoscope light source has been used empirically as the light source for illuminating the abdominal cavity in the laparoscopic surgery. Therefore, if these light sources are suddenly replaced with D65 light sources, many practitioners are expected to experience discomfort from previous experiences.

Medical graphic display system 1000 according to the present invention described in § 2 and color correction device for a medical apparatus 100 used therein assume that shadowless lamp or endoscope light source is used as a light source for illuminating a subject (biotissue) as is conventionally done. Therefore, it is not mandatory to replace the shadowless lamp or endoscope light source with D65 light source. That is, color conversion section for an imaging device 140 illustrated in FIG. 3 may carry out a color conversion to imaging data Dx-Dz imaged under shadowless lamp or endoscope light source, on the assumption that such imaging data are input, and carry out a process of generating standard color graphic data Ds.

However, it is preferred that standard color graphic data Ds obtained by the conversion process by color conversion section for an imaging device 140 are converted so as to be graphic data whose standard color property is the color property that would be obtained under illumination by D65 light source. For example, suppose that in the system illustrated in FIG. 3, medical imaging device 30X is a medical video camera manufactured by Company X provided in surgery room, medical imaging device 30Y is an endoscope camera manufactured by Company Y, and medical imaging device 30Z is an endoscope camera manufactured by Company Z. Further supposing that, imaging data Dx imaged under illumination by shadowless lamp manufactured by Company X is given from medical imaging device 30X, imaging data Dy imaged under illumination by endoscope camera manufactured by Company Y is given from medical imaging device 30Y, and imaging data Dz imaged under illumination by endoscope camera manufactured by Company Z is given from medical imaging device 30Z.

As described above, the spectrum of shadowless lamp and endoscope light source differ from one product to another, and shadowless lamp manufactured by Company X, endoscope light source manufactured by Company Y, and endoscope light source manufactured by Company Z have their peculiar color property respectively, based on the designing specifications of each product provider. As described above, color conversion section for an imaging device 140 is a component carrying out color conversion generating standard color graphic data Ds having a common color property by eliminating the difference of the peculiar color property of each imaging data Dx-Dz. Therefore, as one of the conditions of this common color property, a condition that color property under illumination by D65 light source, is introduced. Thereby, although imaging data Dx is graphic data obtained under illumination by shadowless lamp manufactured by Company X, imaging data Dy is graphic data obtained under illumination by endoscope light source manufactured by Company Y, imaging data Dz is graphic data obtained under illumination by endoscope light source manufactured by Company Z, a color conversion is carried out by conversion process of color conversion section for an imaging device 140 so that any imaging data are converted to a graphic obtained under illumination by D65 light source. By carrying out such color conversion, the graphic finally displayed on the screens of the respective color monitor 50A-50D has a wider color distribution range, and the visibility of the biotissue is improved.

Thus, in order to generate standard color graphic data Ds by carrying out conversion using color property under illumination by D65 light source as the standard color property, conversion data using color property of transmitted light of a predetermined color chart, using light from D65 light source specified by the Commission Internationale de l'eclairage as the background light, as the standard color property may be used as the individual conversion data Cx, Cy, and Cz stored in individual conversion data storage section for an imaging device 110. Specifically, as described in § 3, in the procedure illustrated in FIG. 4, D65 light source may be employed as light source 60.

Certainly, when conversion using color property under illumination by D65 light source as the standard color property is carried out as described above, the tint of biotissue will be different from the tint when it is observed with the direct naked eye. For example, in laparotomy surgery, the practitioner may visually observe biotissue of the laparotomy area under shadowless lamp illumination, directly with naked eye. In this case, the tint of the biotissue observed by the naked eye and the tint of the biotissue displayed on the color monitor are different. In other words, the tint of the biotissue displayed on the color monitor will be different from the tint of the actual biotissue under shadowless lamp illumination. Therefore, in terms of faithfully reproducing the tint of the actual biotissue under shadowless lamp illumination and displaying it on a color monitor, a conversion such as "using color property under illumination by D65 light source as the standard color property" has the opposite effect.

However, in the first place, there is no absolute criterion of "tint of actual biotissue". That is, the tint of the biotissue being visually observed during surgery is simply the tint under illumination by shadowless lamp, a specific product provided by a specific provider, and the tint will be different if the shadowless lamp is replaced by another product. Also, in laparoscopic surgery, the actual biotissue may not be visually observed in the first place, so there is no way to confirm "the tint of the actual biotissue". In view of this, it will be appreciated that it is not as meaningful to faithfully reproduce the tint, obtained under illumination by a specific shadowless lamp or a specific endoscope light source, on a color monitor.

Therefore, in practical use, it is preferable to carry out a conversion using the color property under illumination by D65 light source as a standard color property to generate standard color graphic data Ds. The tint of graphic displayed on the color monitor based on such standard color graphic data Ds is slightly different from the tint of the graphic observed under the illumination by shadowless lamp or endoscope light source. However, there is no particular discomfort. For example, in the case of the example illustrated in FIG. 15, the "original color distribution" occupies a region from a red color to an orange color having a high saturation, whereas, from the red color to the orange color, the "color distribution after conversion" occupies a region spreading from the high saturation to the low saturation, and a large change in hue does not occur.

The first reason why using D65 light source as a light source giving a standard color property (that is, using D65 light source as light source 60 illustrated in FIG. 4) is preferred in implementing the present invention is that the tint (emission spectrum) of shadowless lamp and endoscope light source differs for each individual provider or individual product, whereas the tint (emission spectrum) of D65 light source is unified as defined by the Commission Internationale de l'eclairage (CIE). Therefore, when the tint of standard color graphic data Ds is set based on D65 light source, a display graphic that meets the tint of a unified D65 light source may be obtained on color monitors 50A-50D at all times, regardless of the provider and the product of the shadowless lamp and endoscope light source used as the light source for obtaining respective imaging data Dx, Dy, and Dz.

The second reason is that, by using D65 light source as a light source giving a standard color property, the distribution range of color may be widened, and visibility may be improved. As described above with reference to the measurement results in FIGS. 13-15, the relation "under illumination by shadowless lamp"<"under illumination by endoscope light source"<"under illumination by D65 light source" has been obtained with respect to the broadness of the distribution range of colors. For this reason, when color property under illumination by D65 light source is set as the standard color property, the distribution range of the color on graphic obtained on the color monitor will be widened and visibility may be improved. For example, even in a biotissue having a hue of the identical orange color, a portion having a higher saturation and a portion having a lower saturation are displayed separately on the color monitor, so that the respective portions are easily visually distinguished from each other.

<<<§ 6. Specific Example of Color Conversion for Highlighting a Specific Tissue>>>

In § 2.2 described above, the basic operation of color conversion section for highlighting a specific tissue 160 in color correction device for a medical apparatus 100 illustrated in FIG. 3 has been described as the "basic operation relating second conversion process". In this basic operation, three types of conversion data for highlighting a specific tissue, namely, blood vessel highlighted data Ce for carrying out color conversion highlighting blood vessel, fat highlighted data Cf for carrying out color conversion highlighting fat, and surface layer highlighted data Cg for carrying out color conversion highlighting surface layer are stored in conversion data storage section for highlighting a specific tissue 120, and color conversion section for highlighting a specific tissue 160 carries out color conversion highlighting a specific biotissue to standard color graphic data Ds using these converted data, and generation of specific tissue highlighted graphic data De, Df, and Dg. A substance of these conversion data for highlighting specific tissue Ce, Cf, and Cg and an actual example of "highlighting display" of a specific biotissue will be described here in more detail.

Generally, various biotissue constituting the human body have respective peculiar tint, and the practitioner may recognize many biotissue by the naked eye by distinguishing them from each other. For example, when the human colon is viewed, a plurality of biotissue such as blood vessels, fats, and surface layers may be observed there. FIGS. 13-15 are diagrams illustrating color distributions of each portion of the colon sample itself, and the individual points plotted here indicate the color of the various biotissue constituting the colon.

Figure 16:
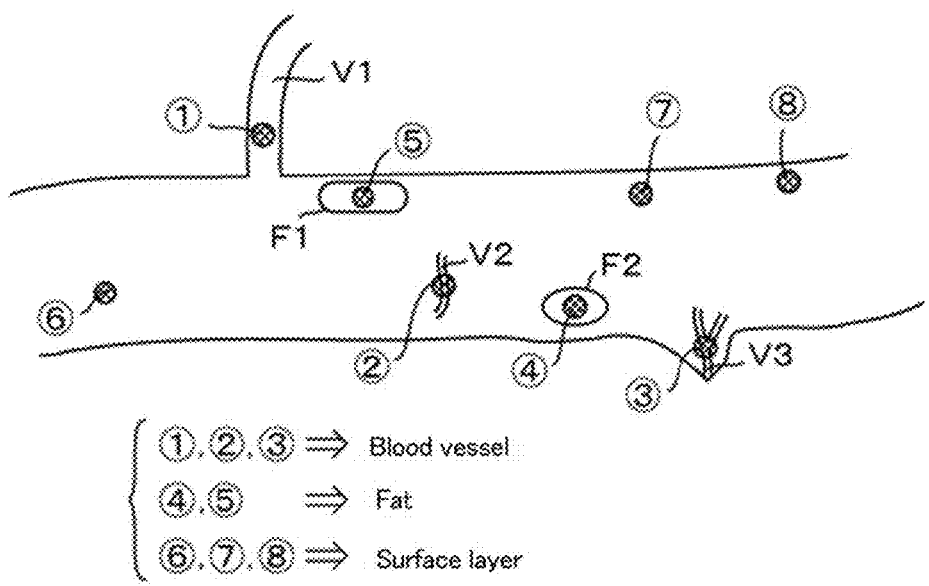
FIG. 16 is a top view illustrating sample locations of the colon sample and its specific tissue used for the measurement in FIG. 13.

FIG. 16 is a top view illustrating sample locations of the colon sample and its specific tissue used for the measurement of the color distribution diagram illustrated in FIGS. 13-15. As illustrated in the figures, the colon sample includes biotissue such as blood vessel portions V1, V2, and V3 and fat portions F1 and F2, in addition to the main body portion constituting the colon main body. Therefore, the inventors of the present application have determined a plurality of sample locations on this colon sample, and have directly measured the colors of individual sample locations using a spectroscopic analyzer. The regions indicated by circled numerals 1-8 in FIG. 16 (hatched circular regions) indicate the respective sample locations. Specifically, the regions indicated by the circled numerals 1-3 indicate the sample locations for the blood vessel portion, the regions indicated by the circled numerals 4-5 indicate the sample locations for the fat portion, and the regions indicated by the circled numerals 6-8 indicate the sample locations for the surface layer portion.

Figure 17:
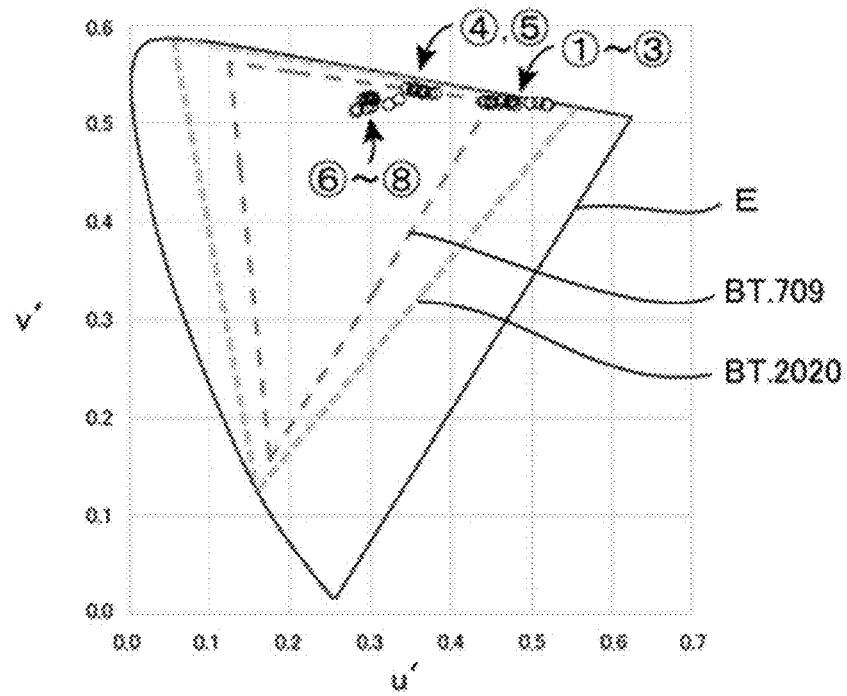
FIG. 17 is a u'v' chromaticity diagram illustrating the color distribution obtained by measuring each sample location illustrated in FIG. 16 under a shadowless lamp.
Figure 18:
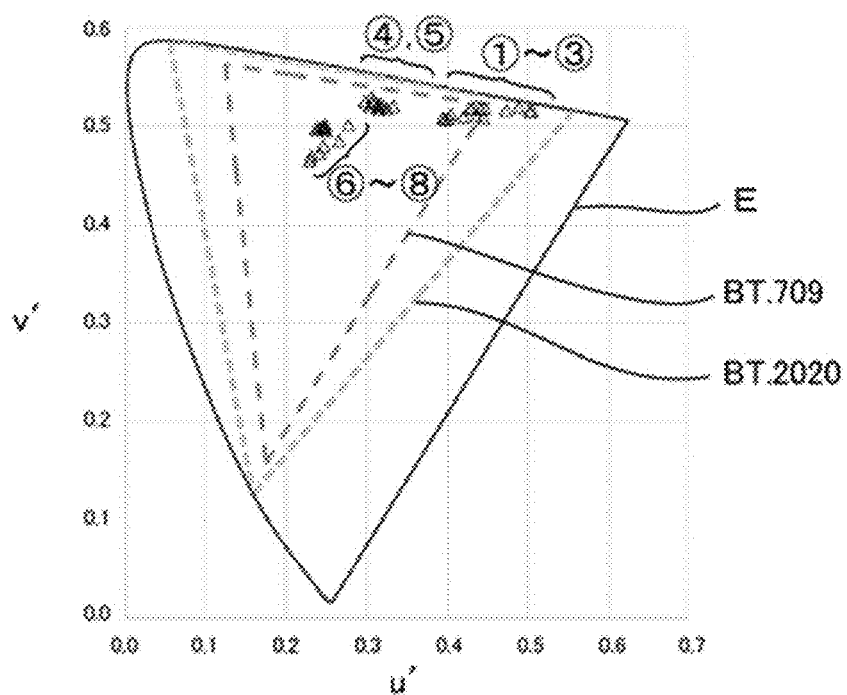
FIG. 18 is a u'v' chromaticity diagram illustrating the color distribution obtained by measuring each sample location illustrated in FIG. 16 under D65 light source.

FIG. 17 is a u'v' chromaticity diagram illustrating the color distribution obtained by measuring each sample location illustrated in FIG. 16 under a shadowless lamp, and FIG. 18 is a u'v' chromaticity diagram illustrating the color distribution obtained by measuring each sample location illustrated in FIG. 16 under D65 light source. The circled numerals 1-8 illustrated in these u'v' chromaticity diagrams correspond to each sample location indicated by the circled numerals 1-8 in FIG. 16. It may be understood from FIGS. 17 and 18 that the individual sample locations each have a peculiar tint. Specifically, the sample locations of the blood vessel portion indicated by the circled numerals 1-3 express red color with high saturation, the sample locations of the fat portion indicated by the circled numerals 4-5 express orange color with high saturation, and the sample locations of the surface layer portion indicated by the circled numerals 6-8 express orange color with slightly lower saturation.

As described in § 5, even for the identical colon sample, the observed tint differs according to the light source used for illumination, and when illuminated with D65 light source (FIG. 18), the distribution range of colors is widened compared to a case illuminated with shadowless lamp (FIG. 17). In FIG. 17 and FIG. 18, by comparing the distribution ranges of the colors for the identical sample locations, it may be understood that the latter is wider than the former. As described above, when the distribution range of colors is widened in this way, it is possible to express the identical biotissue using a larger number of colors, and thus an advantage of improving the visibility may be obtained, as already described in § 5. Therefore, the following will continue the descriptions with reference to the result of illumination with D65 light source (FIG. 18).

Figure 19A:
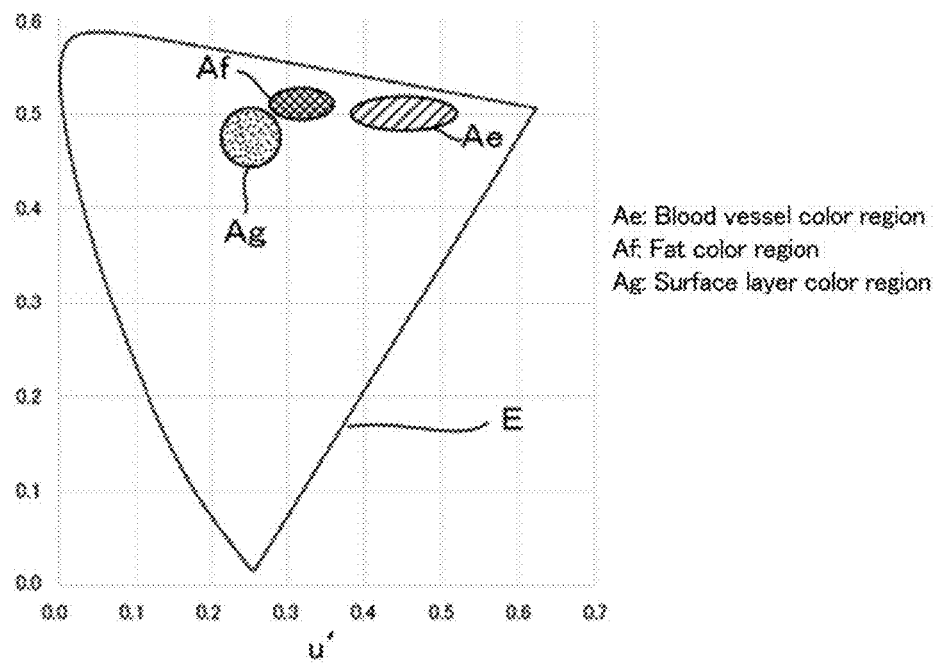
FIGS. 19A and 19B are u'v' chromaticity diagrams illustrating localized color region Ae, Af, and Ag peculiar to a specific biotissue defined by conversion data for highlighting a specific tissue Ce, Cf, and Cg in color correction device for a medical apparatus 100 illustrated in FIG. 3, and its correction direction Me, Mf, and Mg.

FIG. 19A is a u'v' chromaticity diagram illustrating points plotted to indicate individual colors in FIG. 18, grouped by region. That is, in FIG. 19A, the distribution region of the plot group of the blood vessel portion indicated by the circle numerals 1-3 in FIG. 18 is indicated as region Ae, the distribution region of the plot group of the fat portion indicated by the circle numerals 4-5 in FIG. 18 is indicated as region Af, and the distribution region of the plot group of the surface layer portion indicated by the circle numerals 6-8 is indicated as region Ag. Here, these regions Ae, Af, and Ag are referred to as a "localized color region peculiar to a specific biotissue". In other words, color region Ae is localized color region peculiar to blood vessel (blood vessel color region Ae), color region Af is localized color region peculiar to fat (fat color region Af), and color region Ag is localized color region peculiar to the surface layer (surface layer color region Ag).

Thus, for each individual biotissue, considering that the arrangement of the localized color regions in u'v' chromaticity diagram differs, it is possible to estimate which arbitrary point in u'v' chromaticity diagram is the measurement point for which biotissue. For example, for the point plotted within blood vessel color region Ae in FIG. 19A, it may be estimated that it is the measurement point for the sample location belonging to the blood vessel portion. Needless to say, since there are biotissue other than the blood vessel portion, fat portion, and surface layer portion on the colon sample, and there is a case wherein, a color outside of blood vessel color region Ae may be exhibited even for the blood vessel portion. Therefore, the above estimation may not be said to be 100% reliable, but estimation with a certain degree of accuracy may be made by such methods.

As already described in § 2 above, color conversion section for highlighting a specific tissue 160 illustrated in FIG. 3 is a component that carries out color conversion highlighting a specific biotissue designated by a designation input to highlighting tissue designation section 150, to standard color graphic data Ds given from color conversion section for an imaging device 140. However, the color distribution diagram illustrated in FIG. 19A may be used as a diagram illustrating the color distribution of a specific tissue in this standard color graphic data Ds. For example, when a specific biotissue to be highlighted is designated as a "blood vessel", color conversion section for highlighting a specific tissue 160 may select the color in blood vessel color region Ae illustrated in FIG. 19A as the color to be converted in standard color graphic data Ds. As described above, since the color in blood vessel color region Ae may be estimated to be a color exhibited by the blood vessel portion, when the color in blood vessel color region Ae (the pixel having said color) is selected and subjected to the highlighting conversion process, the blood vessel portion may be highlighted and displayed.

Next, a specific example of method for highlighting display will be described. An object of the highlighting display in the present invention is to display a graphic with visibility that is suitable for the examination of a specific biotissue. For example, when the subject is a blood vessel, the practitioner may wish to apply a graphic processing that highlights only the blood vessel and to display a graphic with visibility that is suitable for the examination of the blood vessel. Thus, in order to improve the visibility of the blood vessel, the tint of the blood vessel portion may be changed to a more distinguishing tint so that the blood vessel portion may be clearly distinguished from other biotissue. Generally speaking, to improve visibility of a specific biotissue, the tint of the specific biotissue may be changed to be a more distinguishing tint so that the specific biotissue may be clearly distinguished from other biotissue.

Figure 19B:
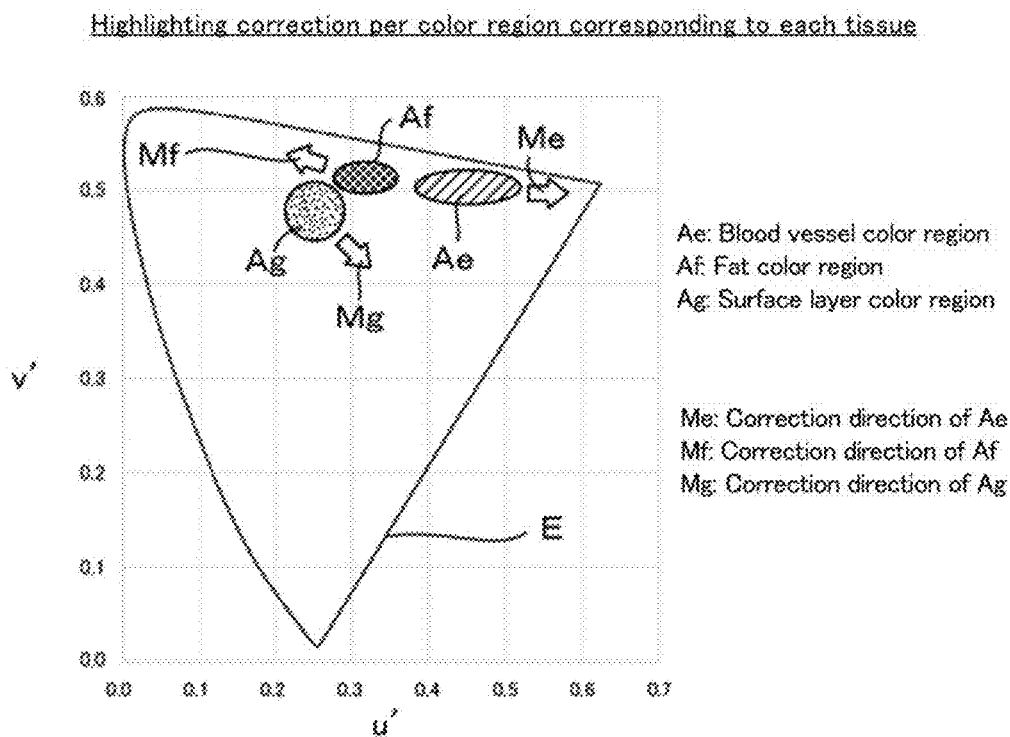

Based on this idea, in the example described here, as a method for a color conversion highlighting a specific biotissue, a process of shifting a color distribution diagram toward a predetermined correction direction, is carried out to a color included in a localized color region on the color distribution diagram corresponding to the specific biotissue. FIG. 19B is a u'v' chromaticity diagram illustrating correction directions Me, Mf, and Mg for the localized color regions Ae, Af, and Ag illustrated in FIG. 19A. Specifically, color conversion processing of shifting the color included in blood vessel color region Ae to correction direction Me is carried out, color conversion processing of shifting the color included in fat color region Af to correction direction Mf is carried out, and color conversion processing of shifting the color included in surface layer color region Ag to correction direction Mg is carried out.

Correction direction Me for blood vessel color region Ae illustrated in FIG. 19B is rightward in u'v' chromaticity diagram, that is, a direction that increases u' value. This means that the color included in blood vessel color region Ae (the color presumed to be exhibited by the blood vessel) is corrected to increase the redness. According to experiments carried out by the inventors of the present application, by carrying out such color correction, visibility of the blood vessel may be improved. The reason therefor is believed that, by carrying out color correction to increase reddish color, the differentiation of the blood vessels with respect to other biotissue was possible.

As a result, in color correction device for a medical apparatus 100 illustrated in FIG. 3, conversion data storage section for highlighting a specific tissue 120 may store, as conversion data for highlighting a specific tissue (blood vessel highlighted data) Ce for carrying out color conversion highlighting the "blood vessel", the conversion data for carrying out the color correction that increases u' value with respect to the color included in the localized color region peculiar to blood vessel, in u'v' chromaticity diagram.

Specifically, as the blood vessel highlighted data Ce, data indicating the localized color region (blood vessel color region) Ae for the blood vessel in FIG. 19B, and data indicating correction direction Me and the correction amount for this blood vessel color region Ae may be prepared. As the data indicating blood vessel color region Ae, for example, data indicating the borderline of region Ae may be used. Also, as the data indicating correction direction Me and the correction amount, for example, the data indicating the correction operation that adds the correction value $\Delta u'e$ may be used. Incidentally in practical use, it is preferable to set the upper limit for the correction values after addition so that the converted data do not protrude real color region E indicated by the solid line in u'v' chromaticity diagram.

Assuming that highlighting tissue designation section 150 receives a designation input to designate "blood vessel" as a specific biotissue to be the subject of the highlighted display, color conversion section for highlighting a specific tissue 160 reads out blood vessel highlighted data Ce from conversion data storage section for highlighting a specific tissue 120, and recognizes blood vessel color region Ae defined by this blood vessel highlighted data Ce. Subsequently, color conversion section for highlighting a specific tissue 160 extracts the pixels of the color included in the recognized blood vessel color region Ae among standard color graphic data Ds given from color conversion section for an imaging device 140, carries out a correction operation that adds the correction value $\Delta u'e$ to the data of the color of the pixel (in practice, a correction that increases or decreases the RGB values is carried out), and outputs the data after the correction operation as specific tissue highlighted graphic data De highlighting the blood vessel.

In the example described above, the correction is carried out by uniformly adding the predetermined correction value $\Delta u'e$ to u' value of the color included in blood vessel color region Ae. However, the correction may be carried out by changing the correction value $\Delta u'e$ in accordance with the original u' value. For example, when the original u' value is small (in the case of the color located on the left-hand side of blood vessel color region Ae illustrated in FIG. 19B), correction value $\Delta u'e$ may be set to be large, and when the original u' value is large (in the case of the color located on the right-hand side of blood vessel color region Ae illustrated in FIG. 19B), correction value $\Delta u'e$ may be set to be small. Further, in the case of the example described above, only u' value is corrected. However, it is also possible to carry out an operation wherein v' value is also corrected as necessary.

Meanwhile, correction direction Mf for fat color region Af illustrated in FIG. 19B is in the upper left direction in u'v' chromaticity diagram, that is, in the direction that decreases u' value as well as increase v' value. This means that the color included in fat color region Af (the color presumed to be exhibited by the fat portion) is corrected in the direction that increases the yellowness while maintaining the saturation. According to experiments carried out by the inventors of the present application, by carrying out such color correction, visibility of the fat may be improved. This is considered to be due to differentiation with respect to other biotissue by carrying out color correction that increases yellowness while maintaining saturation in the fat portion.

Therefore, in color correction device for a medical apparatus 100 illustrated in FIG. 3, as conversion data for highlighting a specific tissue (fat highlighted data) Cf for carrying out color conversion highlight "fat", conversion data storage section for highlighting a specific tissue 120 may store the correction data for carrying out the color correction that decreases u' value as well as increases v' value with respect to the color included in the localized color region peculiar to fat, in u'v' chromaticity diagram.

Specifically, as the fat highlighted data Cf, data indicating the localized color region (fat color region) Af for the fat in FIG. 19B and data indicating correction direction Mf and the correction amount for this fat color region Af may be prepared. As the data indicating fat color region Af, for example, data indicating the borderline of region Af may be used. Also, as the data indicating correction direction Mf and the correction amount, for example, the data indicating the correction operation that subtracts correction value Δu'f as well as adds correction value Δv'f may be used. Again, in practical use, it is preferable to set the upper and lower limits to the correction value after addition and subtraction so that the converted data do not protrude real color region E indicated with the solid line in u'v' chromaticity diagram.

Assuming that highlighting tissue designation section 150 receives a designation input to designate "fat" as a specific biotissue to be the subject of the highlighted display, color conversion section for highlighting a specific tissue 160 reads out fat highlighted data Cf from conversion data storage section for highlighting a specific tissue 120, and recognizes fat color region Af defined by this fat highlighted data Cf. Subsequently, color conversion section for highlighting a specific tissue 160 extracts the pixels of the color included in the recognized fat color region Af among standard color graphic data Ds given from color conversion section for an imaging device 140, carries out a correction operation that subtracts correction value Δu'f as well as adds correction value Δv'f (in practice, a correction is carried out to increase or decrease the RGB value.) to the data of the color of the pixel, and outputs the data after the correction operation as specific tissue highlighted graphic data Df wherein fat is highlighted.

Also in this example, instead of uniformly subtracting the predetermined correction value Δu'f or adding the correction value Δv'f to u' value and v' value of the color included in fat color region Af, an operation may be carried out wherein correction values Δu'f and Δv'f are changed in accordance with the original u' value and the v' value.

Similarly, correction direction Mg for surface layer color region Ag illustrated in FIG. 19B is the lower right direction in u'v' chromaticity diagram, that is, the direction that increases u' value as well as decreases v' value. This means that the color included in surface layer color region Ag (the color presumed to be exhibited by the surface layer portion) is corrected to the direction that increases the redness while decreases the saturation. According to experiments carried out by the inventors of the present application, by carrying out such color correction, the visibility of the surface layer may be improved. This is considered to be due to differentiation with respect to other biotissue by carrying out color correction that increases redness while decreasing saturation in the surface layer portion.

Therefore, in color correction device for a medical apparatus 100 illustrated in FIG. 3, as conversion data for highlighting a specific tissue (surface layer highlighted data) Cg for carrying out color conversion highlighting the "surface layer", conversion data storage section for highlighting a specific tissue 120 may store the converted data for carrying out the color correction that increases u' value as well as decreases v' value with respect to the color included in the localized color region peculiar to the surface layer, in u'v' chromaticity diagram.

Specifically, as the surface layer highlighted data Cg, data indicating the localized color region (surface layer color region) Ag for the surface layer in FIG. 19B, and data indicating correction direction Mg and the correction amount for this surface layer color region Ag may be prepared. As the data indicating surface layer color region Ag, for example, data indicating the borderline of region Ag may be used. Also, as the data indicating correction direction Mg and the correction amount, for example, the data indicating the correction operation that adds correction value Δu'g as well as subtracts correction value Δv'g may be used. Again, in practical use, it is preferable to set the upper and lower limits to the correction value after addition and subtraction so that the converted data do not protrude real color region E indicated with the solid line, in u'v' chromaticity diagram.

Assuming that highlighting tissue designation section 150 receives a designation input to designate "surface layer" as a specific biotissue to be the subject of the highlighted display, color conversion section for highlighting a specific tissue 160 reads out the surface layer highlighted data Cg from conversion data storage section for highlighting a specific tissue 120, and recognizes surface layer color region Ag defined by the surface layer highlighted data Cg. Subsequently, color conversion section for highlighting a specific tissue 160 extracts the pixels of the color included in the recognized surface layer color region Ag among standard color graphic data Ds given from color conversion section for an imaging device 140, carries out a correction operation that adds correction value Δu'g as well as subtracts correction value Δv'g (in practice, the correction that increases or decreases the RGB value is carried out) to the data of the color of the pixel, and outputs the data after the correction operation as specific tissue highlighted graphic data Dg highlighting the surface layer.

Also in this example, instead of uniformly adding a predetermined correction value Δu'g or subtracting correction value Δv'g with respect to u' value and v' value of the color included in surface layer color region Ag, an operation may be carried out wherein correction values Δu'g and Δv'g are changed in accordance with the original u' value and the v' value.

As described above, color correction device for a medical apparatus 100 illustrated in FIG. 3 has a function of carrying out color conversion highlighting a specific biotissue to a graphic data (standard color graphic data Ds) whose subject is a biotissue group, and conversion data storage section for highlighting a specific tissue 120 stores conversion data for highlighting a specific tissue Ce, Cf, and Cg for carrying out color conversion highlighting a specific biotissue. When highlighting tissue designation section 150 receives a designation input designating a specific biotissue to be the subject of the highlighted display, color conversion section for highlighting a specific tissue 160 carries out color conversion, to graphic data obtained based on imaging by the medical imaging device (that is, standard color graphic data Ds obtained based on imaging data Dx, Dy, and Dz), using conversion data for highlighting a specific tissue Ce, Cf, and Cg to carry out color conversion highlighting a specific biotissue designated by a designation input stored in conversion data storage section for highlighting a specific tissue 120 to generate specific tissue highlighted graphic data De, Df, and Dg.

Generally speaking, conversion data for highlighting a specific tissue Ce, Cf, and Cg stored in conversion data storage section for highlighting a specific tissue 120 are data for carrying out a specific color correction to a color included in a localized color region peculiar to a specific biotissue, in a predetermined color space. Here, a three-dimensional color space may be used as the predetermined color space. In this case, a three-dimensional region in a three-dimensional color space is set as the localized color region peculiar to a specific biotissue, and a predetermined direction in the three-dimensional space is set as a correction direction of the color.

In the example described above, a two-dimensional color space is used as a predetermined color space in order to carry out color conversion to hue and saturation by color conversion section for highlighting a specific tissue 160. In other words, conversion data for highlighting a specific tissue Ce, Cf, and Cg are data for carrying out color correction that increases or decreases an abscissa value or an ordinate value, or both, with respect to a color included in a localized color region peculiar to a specific biotissue, in a predetermined two-dimensional chromaticity diagram. In particular, in the example illustrated in FIGS. 19A and 19B, since u'v' chromaticity diagram is employed as the two-dimensional chromaticity diagram, conversion data for highlighting a specific tissue Ce, Cf, and Cg are data for carrying out color correction that increases or decreases u' value or v' value, or both, with respect to the color included in a localized color region peculiar to a particular biotissue, in u'v' chromaticity diagram. Certainly, a chromaticity diagram other than u'v' chromaticity diagram (for example, a xy chromaticity diagram) may be used as the two-dimensional chromaticity diagram.

Meanwhile, when a three-dimensional color space is used as a color space for carrying out color conversion by color conversion section for highlighting a specific tissue 160, a color correction may be carried out wherein a part or all of a three-dimensional coordinate value is increased or decreased, with respect to a color included in the localized color region peculiar to each biotissue (three-dimensional region). For example, in a two-dimensional u'v' chromaticity diagram, only the hue and saturation distributions may be illustrated. However, the color distributions for the three elements of hue, saturation, and brightness may be illustrated with one point (u', v', L) in the three-dimensional color space by, to the u'v' chromaticity diagram, adding the brightness axis L orthogonal to this u'v' chromaticity diagram, and defining the Lu'v' space (three-dimensional color space). Therefore, for a color included in localized color region peculiar to a specific biotissue (three-dimensional region), the biotissue may be highlighted by carrying out a color correction that increases or decreases not only u' value and v' value but also L value. That is, not only the color difference in hue and saturation may be highlighted, but also the difference in brightness may further be highlighted. As described above, since visual differentiation between a specific biotissue and another biotissue may be carried out also with respect to the brightness, visibility of the specific biotissue may be further improved.

When color conversion is carried out in such Lu'v' space, a stereoscopic three-dimensional region may be defined as each localized color region Ae, Af, and Ag illustrated in FIG. 19B, a three-dimensional direction to which L-axis components are added respectively may be set as each correction direction Me, Mf, and Mg, and a correction may be carried out so that the brightness difference between each biotissue and another tissue is highlighted. Specifically, correction that increases u' value, at least, (correction that increases or decreases v' value or L value may be carried out may be carried out to the color included in blood vessel color region Ae; correction that decreases u' value and increases v' value, at least, (correction that increases or decreases L value may be carried out) may be carried out to the color included in fat color region Af; and correction that increases u' value and decreases v' value, at least, (correction that increases or decreases L value may be carried out) may be carried out to the color included in surface layer color region Ag.

Certainly, the three-dimensional color space for carrying out color conversion by color conversion section for highlighting a specific tissue 160 is not limited to the above-mentioned Lu'v' space; and for example, the HLS space in the HLS color model or the HSV space in the HSV color model may be used. In this case, the respective correction direction Me, Mf, and Mg, will be set in the appropriate direction, respectively according to the three-dimensional color space to be used.

FIGS. 19A and 19B illustrate an example using specific conversion data for three types of biotissues of blood vessel, fat, and surface layer, as conversion data for highlighting a specific tissue. In this example, highlighting tissue designation section 150 has a function of receiving designation input designating "blood vessel" as a specific biotissue to be the subject of the highlighted display, and as conversion data for highlighting a specific tissue Ce for carrying out color conversion highlighting "blood vessel", conversion data storage section for highlighting a specific tissue 120 stores, conversion data for carrying out color correction that increases u' value, at least, with respect to the color included in the localized color region peculiar to blood vessel Ae, in u'v' chromaticity diagram (or may be Lu'v' space).

In this example, highlighting tissue designation section 150 has a function of receiving designation input designating "fat" as a specific biotissue to be the subject of the highlighted display, and as conversion data for highlighting a specific tissue Cf for carrying out color conversion highlighting "fat", conversion data storage section for highlighting a specific tissue 120 stores, conversion data for carrying out color correction that decreases u' value as well as increases v' value, at least, with respect to the color included in the localized color region peculiar to fat Af, in u'v' chromaticity diagram (or may be Lu'v' space).

Further, in this example, highlighting tissue designation section 150 has a function of receiving designation input designating "surface layer" as a specific biotissue to be the subject of the highlighted display, and as conversion data for highlighting a specific tissue Cg for carrying out color conversion highlighting "surface layer", conversion data storage section for highlighting a specific tissue 120 stores, conversion data for carrying out color correction that increases u' value as well as decreases v' value, at least, with respect to the color included in the localized color region peculiar to surface layer Ag, in u'v' chromaticity diagram (or may be Lu'v' space).

Figure 20:
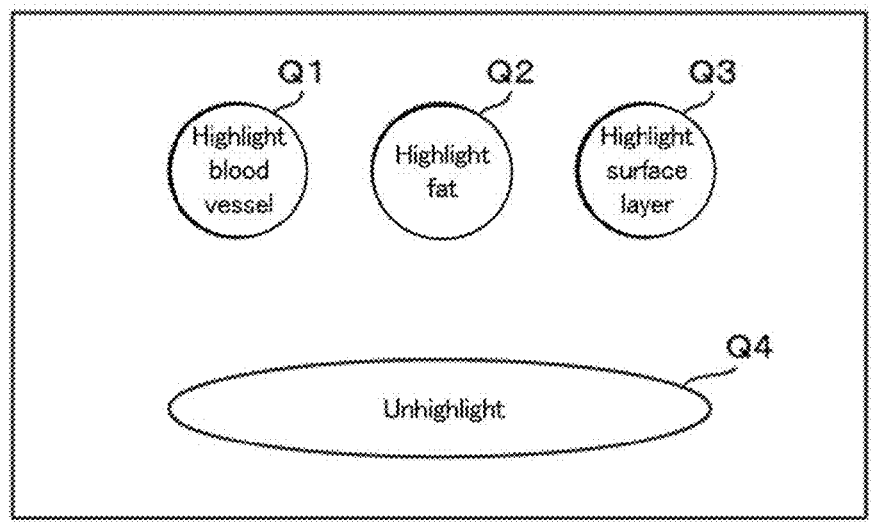
FIG. 20 is a front view illustrating an example of instruction button constituting highlighting tissue designation section 150 in color correction device for a medical apparatus 100 illustrated in FIG. 3.

FIG. 20 is a front view illustrating an example of instruction button constituting highlighting tissue designation section 150 in color correction device for a medical apparatus 100 illustrated in FIG. 3. The example illustrated here is an example wherein highlighting tissue designation section 150 has an inputting function for designating "blood vessel", "fat" and "surface layer" as a specific biotissue to be the subject of the highlighted display. As illustrated, highlighting tissue designation section 150 is provided with blood vessel highlighting instruction button Q1, fat highlighting instruction button Q2, surface layer highlighting instruction button Q3, and unhighlighting button Q4. In this highlighting tissue designation section 150, since the empty designation condition wherein no biotissue is designated as the subject of the highlighted display, is defaulted, when the operator does not operate anything, it is processed as the "empty designation input" is input, and color conversion section for highlighting a specific tissue 160 outputs the input standard color graphic data Ds as it is, without carrying out any substantial color conversion process.

The operator may press blood vessel highlighting instruction button Q1 to highlight the "blood vessel", press fat highlighting instruction button Q2 to highlight the "fat", and press surface layer highlighting instruction button Q3 to highlight the "surface layer". When unhighlighting button Q4 is pressed, the highlighting designations for all the biotissues are canceled. Also, in this highlighting tissue designation section 150, a plurality of biotissues may be designated in an overlapping manner. For example, when the operator wishes to highlight both the "blood vessel" and the "fat", the pressing operation of blood vessel highlighting instruction button Q1 and the pressing operation of fat highlighting instruction button Q2 may be carried out in an overlapping manner. In this case, color conversion section for highlighting a specific tissue 160 carries out color conversion using blood vessel highlighted data Ce and color conversion using fat highlighted data Cf to standard color graphic data Ds in an overlapping manner, and outputs specific tissue highlighted graphic data Def. Specifically, in FIG. 19B, the color included in blood vessel color region Ae is color-corrected to correction direction Me, and the color included in blood vessel color region Af is color-corrected to correction direction Mf. When there is an overlapping portion in the localized color regions of a plurality of biotissues designated in an overlapping manner, the overlapping color correction is carried out to the colors in the overlapping portion, but no particular problems arise.

When color correction device for a medical apparatus 100 is configured using a computer, highlighting tissue designation section 150 illustrated in FIG. 20 may be realized using a display for computer operation. That is, an input screen illustrated in FIG. 20 may be displayed on a display for computer operation, and an input operation by a touchscreen or an input operation by a pointing device such as a mouse may be carried out to recognize a pressing instruction for each of the buttons Q1-Q4. Further, as in the example illustrated in FIG. 3, in the case of a system wherein a plurality of color monitors 50A-50D are connected, graphic display wherein different biotissue is highlighted respectively may be carried out for each color monitor. However, in this case, designation inputs illustrated in FIG. 20 may be carried out for each color monitor (for example, monitor designation buttons for designating a color monitor to display may be provided).

As biotissue to be the subject of a highlighted display, examples have been described above wherein three types of "blood vessel", "fat" and "surface layer" may be processed. However, various types of biotissues such as "bone", "cartilage" and "muscle" may be the subject of the highlighted display, besides the above.

Figure 21:
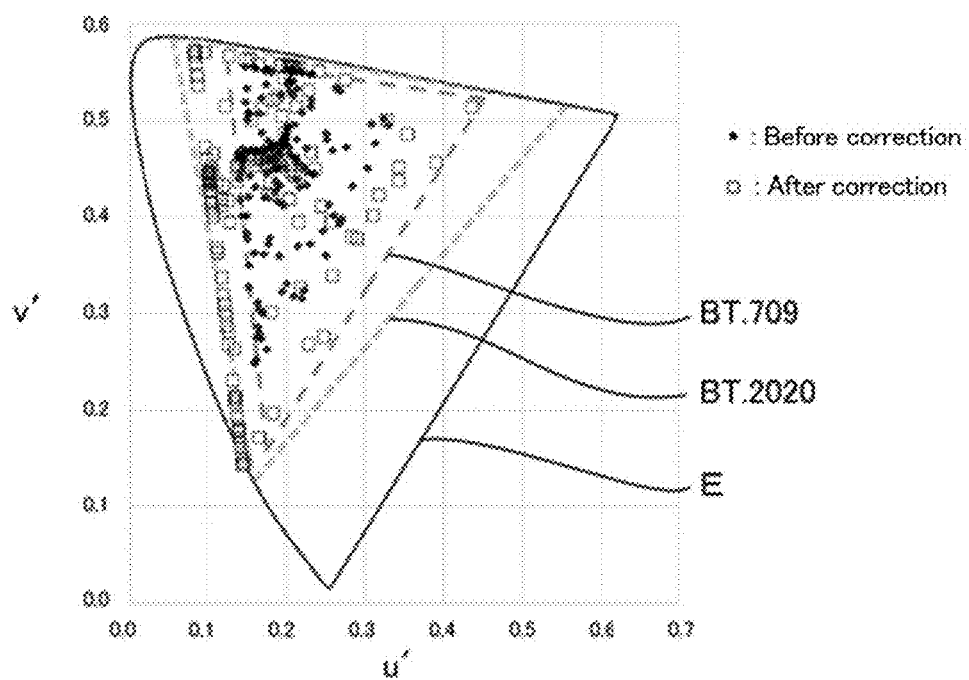
FIG. 21 is a u'v' chromaticity diagram illustrating the color distribution of the graphic data obtained by carrying out various highlighting correction by color conversion section for highlighting a specific tissue 160, to graphic data having the color distribution illustrated in FIG. 10.

FIG. 21 is a u'v' chromaticity diagram illustrating the color distribution of the graphic data obtained by carrying out various highlighting correction (wherein highlighting color conversion to some other biotissues is added to the highlighting color conversion to "blood vessel", "fat", and "surface layer" illustrated in FIGS. 19A and 19B) by color conversion section for highlighting a specific tissue 160, to graphic data having the color distribution illustrated in FIG. 10 (graphic data including color sample of various color charts 70). Black dots illustrated in FIG. 21 indicate the color distribution before correction, and white squares indicate the color distribution after correction. In the example illustrated in FIG. 21, since color chart 70 is used as the subject instead of the actual biotissue, the color (black dots) before correction is also distributed in a wide range to some extent. However, by carrying out color conversion correction by color conversion section for highlighting a specific tissue 160, it is understood that the distribution range of the color (white squares) after correction is further expanded.

As described above, when displaying on the color monitor, when a correction that widens the color distribution range is carried out, individual biotissue may be expressed with more colors, and the effect of improving the visibility as a whole may be obtained.

REFERENCE SIGNS LIST

10: surgical table
20: shadowless lamp
30: medical imaging device (such endoscope camera)
30X, 30Y, 30Z: medical imaging device (such as endoscope camera)
31: endoscope camera
40: imaging control unit
41: endoscope control unit
50: color monitor
50A, 50B, 50C, 50D: color monitor
51-54: color monitor
60: light source (D65 light source)
70: color chart
71: three primary color chart
72: multicolor chart
73: wide gamut color chart
80: individual conversion data preparation section
90: spectroscopic analyzer
100: color correction device for a medical apparatus
110: individual conversion data storage section for an imaging device
120: conversion data storage section for highlighting a specific tissue
130: individual conversion data storage section for a monitor
140: color conversion section for an imaging device
150: highlighting tissue designation section
160: color conversion section for highlighting a specific tissue
170: color conversion section for a monitor
1000: medical graphic display system
Ae: blood vessel color region (localized color region peculiar to blood vessel)
Af: fat color region (localized color region peculiar to fat)
Ag: surface layer color region (localized color region peculiar to the surface layer)
B, BB: blue point in u'v' chromaticity diagram B-new: blue component of color data after conversion
B-old: blue component of color data before conversion
BT: blue component of original color data
Bt: blue component of imaging color data
BT.709: triangle indicating color region specified in international specification of BT.709
BT.2020: triangle indicating color region specified in international specification of BT.2020
Ca, Cb, Cc, Cd: individual conversion data for a monitor
Ce: conversion data for highlighting a specific tissue (blood vessel highlighted data)
Cf: conversion data for highlighting a specific tissue (fat highlighted data)
Cg: conversion data for highlighting a specific tissue (surface layer highlighted data)
Cx, Cy, Cz: individual conversion data for an imaging device
Da, db, Dc, Dd: display data
De, Df, Dg: specific tissue highlighted graphic data
Dp: imaging data
Ds: standard color graphic data
Dsp1, Dsp2: spectral data
DT: original color data
Dt: imaging color data
Dx, Dy, Dz: imaging data
E: real color region
F1, F2: fat region
f1, f2, f3: mathematical function for conversion
G, GG: green point in u'v' chromaticity diagram
G1: visible light spectrum of a shadowless lamp/color temperature point in u'v' chromaticity diagram
G2: visible light spectrum of an endoscope light source (via fiber)
G3: visible light spectrum of an endoscope light source (direct)/color temperature point in u'v' chromaticity diagram
G4: visible light spectrum of D65 light source/color temperature point in u'v' chromaticity diagram
G5: visible light spectrum of D50 light source/color temperature point in u'v' chromaticity diagram
G-new: green component of color data after conversion
G-old: green component of color data before conversion
GT: green component of original color data
Gt: green component of imaging color data
l, l': red component of color data
LUT: lookup table
M: color distribution region on a monitor screen
Me: correction direction for blood vessel color region Ae
Mf: correction direction for fat color region Af
Mg: correction direction for surface layer color region Ag
m, m': green component of color data
n, n': blue component of color data
P: subject (patient)
P1: actual organ
P2: display graphic of organ
Q1: blood vessel highlighting instruction button
Q2: fat highlighting instruction button
Q3: surface layer highlighting instruction button
Q4: unhighlighting button
R, RR: red point in u'v' chromaticity diagram
RT: red component of original color data
Rt: red component of imaging color data
R-old: red component of color data before conversion
R-new: red component of color data after conversion
u': abscissa axis in u'v' chromaticity diagram
V1, V2, V3: blood vessel region
v': ordinate axis in u'v' chromaticity diagram
W: white point in u'v' chromaticity diagram

The invention claimed is:

1. A color correction device for a medical apparatus configured to carry out a color correction, appropriate for a display on a color monitor, to graphic data obtained by imaging with a medical imaging device, the color correction device for a medical apparatus comprising:
an individual conversion data storage section for an imaging device configured to store individual conversion data for converting a color property of imaging data imaged by a specific medical imaging device into a standard color property, in consideration of a peculiar color property of the medical imaging device,
a conversion data storage section for highlighting a specific tissue configured to respectively store conversion data for highlighting a specific tissue for a plurality of J types of biotissues for carrying out color conversion highlighting a specific biotissue, wherein the conversion data for highlighting a specific tissue are data for carrying out a specific color correction, to a color included in a localized color region peculiar to a specific biotissue, in a predetermined color space,
an individual conversion data storage section for a monitor configured to store individual conversion data for carrying out color conversion such that a graphic having a standard color property is displayed on a specific color monitor, in consideration of a peculiar color property of the color monitor,
a color conversion section for an imaging device configured to generate standard color graphic data by carrying out color conversion, to the imaging data input from the specific medical imaging device, using individual conversion data for the specific medical imaging device stored in the individual conversion data storage section for an imaging device,
a highlighting tissue designation section configured to receive a designation input designating a specific biotissue to be highlighted,
a color conversion section for highlighting a specific tissue configured to:
receive a designation input designating a j-th ($1 \leq j \leq J$) biotissue from the highlighting tissue designation section, and
generate specific tissue highlighted graphic data by carrying out color conversion, to the standard color graphic data, using a j-th conversion data for highlighting a specific tissue, wherein the color conversion converts the color included in the localized color region peculiar to the specific biotissue into another color, and
a color conversion section for a monitor configured to generate display data by carrying out color conversion, to the specific tissue highlighted graphic data, using the individual conversion data for the specific color monitor stored in the individual conversion data storage section for a monitor, and to output the generated display data to the specific color monitor.

2. The color correction device for a medical apparatus according to claim 1, wherein the individual conversion data stored in the individual conversion data storage section for an imaging device are conversion data capable of converting a color to a color that covers a wide color gamut of a specification specified in international specification BT.2020 for ultra-high-definition television.

3. The color correction device for a medical apparatus according to claim 1, wherein the individual conversion data stored in the individual conversion data storage section for an imaging device are conversion data using a color property of transmitted light of a predetermined color chart, employing light from D65 light source specified by Commission Internationale de l'eclairage as a background light, as a standard color property.

4. The color correction device for a medical apparatus according to claim 1, wherein the individual conversion data stored in the individual conversion data storage section for an imaging device are conversion data for converting three primary color components R-old, G-old, and B-old of the imaging data into three primary color components R-new, G-new, and B-new of the standard color graphic data.

5. The color correction device for a medical apparatus according to claim 1,
wherein the individual conversion data for a plurality of I medical imaging devices are stored respectively in the individual conversion data storage section for an imaging device, and
to the imaging data input from an i-th (1≤i≤I) medical imaging device, the color conversion section for an imaging device carries out color conversion using an i-th individual conversion data so as to generate a standard color graphic data.

6. The color correction device for a medical apparatus according to claim 1, wherein the color conversion section for an imaging device inputs the imaging data imaged under a shadowless lamp or an endoscope light source, and generates a standard color graphic data by carrying out a color conversion thereto.

7. The color correction device for a medical apparatus according to claim 1, wherein the individual conversion data stored in the individual conversion data storage section for an imaging device include a lookup table configured to convert a combination of each color component constituting the imaging data into a combination of each color component constituting standard color graphic data.

8. The color correction device for a medical apparatus according to claim 1, wherein the individual conversion data stored in the individual conversion data storage section for an imaging device include a mathematical function configured to calculate a combination of each color component constituting standard color graphic data, by giving a combination of each color component constituting the imaging data, as a variable value.

9. The color correction device for a medical apparatus according to claim 1, wherein the highlighting tissue designation section has a function of receiving an empty designation input indicating that none of the biotissue is designated, and
when the color conversion section for highlighting a specific tissue receives the empty designation input from the highlighting tissue designation section, the standard color graphic data is output as they are, as the specific tissue highlighted graphic data, without carrying out a color conversion.

10. The color correction device for a medical apparatus according to claim 1, wherein the conversion data for highlighting a specific tissue stored in the conversion data storage section for highlighting a specific tissue are data for carrying out color correction that increases or decreases an abscissa value or an ordinate value, or both, with respect to a color included in a localized color region peculiar to a specific biotissue, in a predetermined two-dimensional chromaticity diagram.

11. The color correction device for a medical apparatus according to claim 10, wherein the conversion data for highlighting a specific tissue stored in the conversion data storage section for highlighting a specific tissue are data for carrying out color correction that increases or decreases u' value or v' value, or both, with respect to a color included in a localized color region peculiar to a specific biotissue, in u'v' chromaticity diagram.

12. The color correction device for a medical apparatus according to claim 11, wherein the highlighting tissue designation section has a function of receiving designation input designating "blood vessel" as a specific biotissue to be a subject of a highlighted display, and
as the conversion data for highlighting a specific tissue for carrying out color conversion highlighting "blood vessel", the conversion data for carrying out color correction that increases u' values with respect to a color included in localized color region peculiar to the blood vessel, in u'v' chromaticity diagram are stored in the conversion data storage section for highlighting a specific tissue.

13. The color correction device for a medical apparatus according to claim 11, wherein the highlighting tissue designation section has a function of receiving designation input designating "fat" as a specific biotissue to be a subject of a highlighted display, and
as the conversion data for highlighting a specific tissue for carrying out color conversion highlighting "fat", the conversion data for carrying out color correction that decreases u' value as well as increases v' value with respect to a color included in localized color region peculiar to the fat, in u'v' chromaticity diagram are stored in the conversion data storage section for highlighting a specific tissue.

14. The color correction device for a medical apparatus according to claim 11, wherein the highlighting tissue designation section has a function of receiving designation input designating "surface layer" as a specific biotissue to be a subject of a highlighted display, and
as the conversion data for highlighting a specific tissue for carrying out color conversion highlighting "surface layer", the conversion data for carrying out color correction that increases u' value as well as decreases v' value with respect to a color included in localized color region peculiar to the surface layer, in u'v' chromaticity diagram are stored in the conversion data storage section for highlighting a specific tissue.

15. A medical graphic display system comprising the color correction device for a medical apparatus according to claim 1, at least one medical imaging device configured to give imaging data to the color correction device for a medical apparatus, and at least one color monitor configured to display a graphic based on display data output from the color correction device for a medical apparatus.

16. A program stored on a non-transitory computer-readable medium and configured to make a computer function as the color correction device for a medical apparatus according to claim 1.

17. A color correction device for a medical apparatus configured to carry out a color correction, appropriate for a display on a color monitor, to graphic data obtained by imaging with a medical imaging device, the color correction device for a medical apparatus comprising:
an individual conversion data storage section for an imaging device configured to store individual conversion data for converting a color property of imaging data imaged by a specific medical imaging device into a standard color property, in consideration of a peculiar color property of the medical imaging device, a conversion data storage section for highlighting a specific tissue configured to store conversion data for highlighting a specific tissue for carrying out color conversion highlighting a specific biotissue, an individual conversion data storage section for a monitor configured to store individual conversion data for carrying out color conversion such that a graphic having a standard color property is displayed on a specific color monitor, in consideration of a peculiar color property of the color monitor, a color conversion section for an imaging device configured to generate standard color graphic data by carrying out color conversion, to the imaging data input from the specific medical imaging device, using individual conversion data for the specific medical imaging device stored in the individual conversion data storage section for an imaging device, a highlighting tissue designation section configured to receive a designation input designating a specific biotissue to be highlighted, a color conversion section for highlighting a specific tissue configured to generate specific tissue highlighted graphic data by carrying out color conversion, to the standard color graphic data, using conversion data for highlighting specific tissue for carrying out color conversion for highlighting a specific biotissue designated by the designation input stored in the conversion data storage section for highlighting a specific tissue, and a color conversion section for a monitor configured to generate display data by carrying out color conversion, to the specific tissue highlighted graphic data, using the individual conversion data for the specific color monitor stored in the individual conversion data storage section for a monitor, and to output the generated display data to the specific color monitor, wherein:

the conversion data for highlighting a specific tissue for a plurality of J types of biotissues are stored respectively in the conversion data storage section for highlighting a specific tissue, and when the color conversion section for highlighting a specific tissue receives a designation input designating a j-th ($1 \leq j \leq J$) biotissue from the highlighting tissue designation section, the color conversion is carried out using a j-th conversion data for highlighting a specific tissue so as to generate specific tissue highlighted graphic data, and the highlighting tissue designation section has a function of receiving designation input designating a plurality of H types ($H \leq J$) of biotissues in an overlapping manner, and when the color conversion section for highlighting a specific tissue receives a designation input designating a plurality of H types of biotissues from the highlighting tissue designation section, the color conversion using a plurality of H types of conversion data for highlighting a specific tissue corresponding to the plurality of H types of biotissues is carried out in an overlapping manner so as to generate the specific tissue highlighted graphic data.

* * * * *